United States Patent
Diaz et al.

(10) Patent No.: US 6,938,488 B2
(45) Date of Patent: Sep. 6, 2005

(54) ACOUSTIC INSPECTION DEVICE

(75) Inventors: Aaron A. Diaz, West Richland, WA (US); Brion J. Burghard, West Richland, WA (US); James R. Skorpik, Kennewick, WA (US); Richard A. Pappas, Richland, WA (US); O. Dennis Mullen, West Richland, WA (US); Todd J. Samuel, Pasco, WA (US); Larry D. Reid, Benton City, WA (US); Joe C. Harris, Kennewick, WA (US); Juan D. Valencia, Richland, WA (US); Jonathan T. Smalley, Battle Ground, WA (US); Chester L. Shepard, West Richland, WA (US); Theodore T. Taylor, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 168 days.

(21) Appl. No.: 10/225,910

(22) Filed: Aug. 21, 2002

(65) Prior Publication Data

US 2004/0035208 A1 Feb. 26, 2004

(51) Int. Cl.[7] .............................................. G01N 29/18
(52) U.S. Cl. .............................. 73/597; 73/52; 73/64.53
(58) Field of Search .......................... 73/597, 632, 644, 73/61.49, 61.75, 61.79, 64.53, 52

(56) References Cited

U.S. PATENT DOCUMENTS

| | | | |
|---|---|---|---|
| 3,608,715 A | 9/1971 | Snyder et al. ............ 209/111.9 |
| 3,802,252 A | 4/1974 | Hayward et al. ............... 73/52 |
| 3,942,381 A | * 3/1976 | Brown et al. .................. 73/597 |
| 4,223,790 A | 9/1980 | Yoshida ....................... 209/590 |
| 4,241,430 A | 12/1980 | Kayem et al. |
| 4,407,293 A | 10/1983 | Suarez, Jr. et al. |
| 4,565,088 A | 1/1986 | Crambes ..................... 73/61.1 |
| 4,584,676 A | 4/1986 | Newman |
| 4,821,573 A | 4/1989 | Nagata et al. ................. 73/597 |
| 5,255,564 A | 10/1993 | Glad et al. ..................... 73/597 |
| 5,404,755 A | 4/1995 | Olson et al. .................. 73/639 |
| 5,457,997 A | 10/1995 | Naruo et al. .................. 73/643 |
| 5,473,934 A | 12/1995 | Cobb ........................ 73/61.49 |
| 5,535,627 A | 7/1996 | Swanson et al. ............. 73/597 |
| 5,559,292 A | 9/1996 | Hull et al. .................... 73/597 |
| 5,568,449 A | 10/1996 | Rountree et al. |
| 5,600,303 A | 2/1997 | Husseiny et al. ........... 340/568 |
| 5,600,700 A | 2/1997 | Krug et al. .................... 378/57 |
| 5,606,130 A | 2/1997 | Sinha et al. .................. 73/627 |
| 5,608,164 A | 3/1997 | MacLauchlan ............... 73/599 |
| 5,616,856 A | 4/1997 | Castel ....................... 73/61.45 |
| 5,619,423 A | 4/1997 | Scrantz |
| 5,690,114 A | 11/1997 | Chiang et al. ......... 128/661.01 |
| 5,692,029 A | 11/1997 | Husseiny et al. ............. 378/88 |
| 5,698,787 A | 12/1997 | Parzuchowski et al. ....... 73/643 |
| 5,754,498 A | 5/1998 | Toda .......................... 367/137 |
| 5,767,407 A | 6/1998 | Sinha .......................... 73/579 |

(Continued)

FOREIGN PATENT DOCUMENTS

EP 0 635 719 A2 1/1995
WO WO 01/94934 A1 12/2001

Primary Examiner—John E. Chapman
(74) Attorney, Agent, or Firm—James D. Matheson

(57) ABSTRACT

An ultrasound inspection apparatus particularly adapted to examine containers (sealed or unsealed) containing a liquid or solid bulk material. The apparatus has an overall configuration of a hand held pistol with a front transducer contact surface that is positioned against a front wall of the container. An ultrasound pulse is transmitted from the apparatus to be reflected from a back wall of a container being investigated. The received echo pulse is converted to a digital waveform. The waveform is analyzed relative to temperature, travel distance of the pulse(s), and time of travel to ascertain characteristics of the liquid or other materials and to provide identification of the same.

55 Claims, 23 Drawing Sheets

U.S. PATENT DOCUMENTS

| | | | |
|---|---|---|---|
| 5,872,314 A | 2/1999 | Clinton | 73/602 |
| 5,929,337 A | 7/1999 | Collins et al. | 73/597 |
| 5,974,111 A | 10/1999 | Krug et al. | 378/57 |
| 5,979,240 A | 11/1999 | Rix et al. | 73/602 |
| 6,029,530 A | 2/2000 | Patton et al. | 73/866.5 |
| 6,216,623 B1 | 4/2001 | Wilkins | |
| 6,234,023 B1 | 5/2001 | Collins et al. | 73/597 |
| 6,247,353 B1 * | 6/2001 | Battenberg et al. | 73/632 |

* cited by examiner

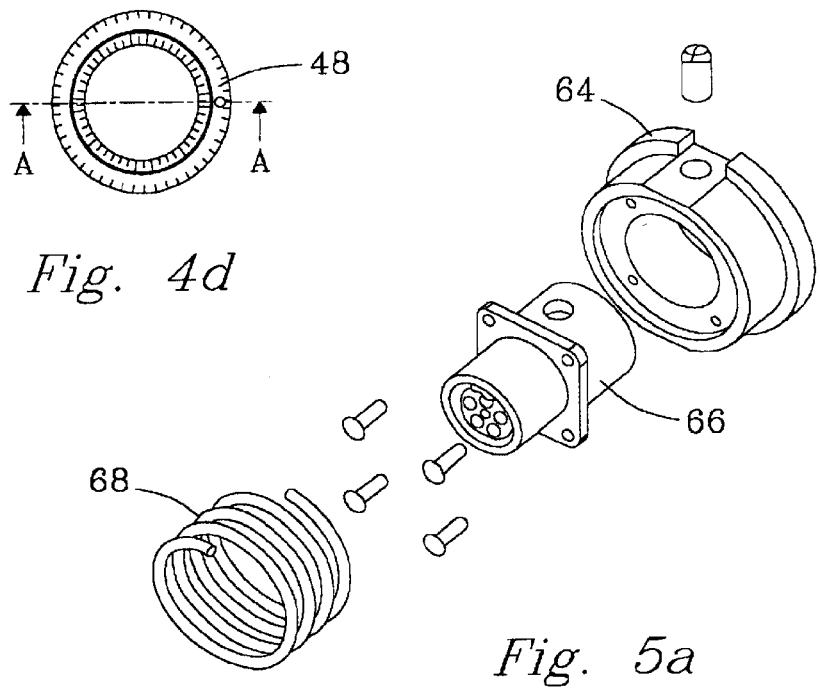
*Fig. 4d*
*Fig. 5a*
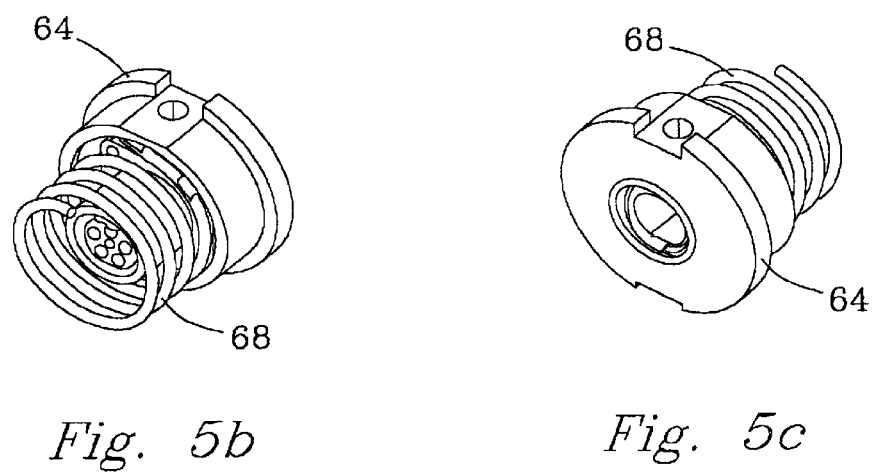
*Fig. 5b*  *Fig. 5c*

Tap "Size" to View Container Types

Oil Drum Inspection

ACOUSTIC INSPECTION DEVICE

This invention was made with Government support under Contract DE-AC0676RLO1830 awarded by the U.S. Department of Energy. The Government has certain rights in the invention.

FIELD OF THE INVENTION

The present invention relates to ultrasound inspection, and more particularly to an apparatus and method for non-intrusive/non-invasive acoustics inspection utilizing ultrasound.

BACKGROUND OF THE INVENTION

There are numerous industries where it is desirable or necessary to ascertain the contents of containers. Both domestic and international applications exist. Domestic applications are replete, for example, in law enforcement, the military, border control, and transport and shipping. In the International community, international border control, training, and treaty convention efforts are significant applications. Other applications include efforts to deter illicit drug manufacturing and smuggling, to collect taxes and tariffs, to effectively maintain inventories, and to verify and ensure treaty compliance. Further, the diversity of needs within any given industry is wide and complex. For example, in industries ranging from foods processing to chemical inventory management, material quality and process control are central to achieving high standards of product performance and safety.

Because of the large number of containers which are shipped both domestically and internationally, including those being transported across domestic and international borders, there is a particular need for a relatively fast and effective way to conduct non-intrusive interrogation of containers. Desirably, this should be able to be accomplished in a manner that not only permits identification of materials within the container (e.g. liquids, solids, bulk materials, etc.), but also ascertains the presence of objects which would not be expected to be in a container. For example, there may be a package containing contraband being smuggled across an international boundary concealed or submerged within a container of liquid or otherwise hidden within a bulk material.

Ultrasound has certain advantages, one of which is that it can easily penetrate dense materials, including liquids, that often defeat x-ray inspection methods. And, therefore, ultrasound has found application in such diverse industries as the medical profession and industrial quality control, in such applications as detecting defects in materials and determining liquid fill levels.

However, there exists a long-standing need to provide an ultrasound system for non-intrusive/non-invasive examination, and/or investigation of a diversity of containers, where the examination can take place conveniently, rapidly, and reliably, and where the overall inspection process is "user friendly". Current systems rely heavily on expensive and time-consuming direct sampling as well as laboratory analysis. From standpoints of purpose, ease of use, cost, size, and flexibility, the embodiments of the present invention are distinctive.

SUMMARY OF THE INVENTION

The present invention is an ultrasonic apparatus suited for non-destructive/non-invasive inspection, interrogation, and investigation of a wide variety and types of containers (both sealed and unsealed) as well as materials within the container. The term "container", as used herein, means a receptacle or other vessel wherein materials of interest are contained in order to be shipped, transported, or otherwise temporarily housed. Examples include open and unsealed drums or receptacles; closed and/or sealed drums or receptacles; open-air containers including hidden panel compartments within automobiles or other vehicles; cargo holds within transport vehicles or ships; receptacles for shipping, containing, or otherwise transporting bulk materials; flow structures and systems including tubing, piping, venting, etc.; process monitoring stations and systems. Also included are the wide diversity of containers used in the shipping and transport industries, including tankers, shipping containers, cargo containers (i.e., comex boxes), open-air cargo holds or other commodity transport compartments. It will also be apparent to those skilled in the art that, in its broader scope, a container may comprise a bulk material wherein a cavity or other chamber may exist. For example, a container may include the range of outwardly innocuous commodity items, such as metal ingots, with hollowed-out chambers, or tar kegs. Alternatively, a container may comprise a 55-gallon drum containing a bulk solid or a liquid wherein a sealed package containing contraband is concealed.

As embodied herein, a container may also comprise both single and multi-compartmented containment vessels. For example, simple containers may comprise at least a front wall and a back wall in order to define in part the receptacle or containing vessel or chamber within a container or otherwise bulk material (e.g., 55-gallon drum, hidden compartment in a vehicle, package of contraband within a bulk material, etc.). More complex containers may comprise a variety of process and/or flow systems or piping used for transporting or shipping materials.

One embodiment of the present invention is an inspection apparatus for the non-intrusive/non-invasive interrogation or investigation of containers, including receptacles, vessels, and various flow systems. The present invention is not only capable of ascertaining types of materials in the containers, but also can non-intrusively detect hidden packages inside cavities of sealed containers. The apparatus may be configured and operated in both a manual and automated mode.

In the manual mode, the present invention is suited for the investigation of containers, vessels, chambers, or systems not easily interrogated or accessible because of size, depth, physical constraints, accessibility problems, commercial loads, physical encumberances, lack of uniform dimensions, or other restrictions. Selection of the best target or location site for manual interrogation of the container is at the discretion of the intended user.

In an automated configuration, the present invention may be used as an inspection apparatus for on-line, real-time monitoring, interrogration and investigation of internal contents in containers used in a variety of processes and flow systems. For example, the inspection device may be attached to the outside of a pipe or included as part of a spool piece surrounding a flow-containment system, thereby allowing the inspection, monitoring, and/or examination of the physical properties of materials flowing through the piping or flow system in real-time. The inspection apparatus may also be used in other related process and/or control systems in real-time, such as monitoring and control applications.

From the preceeding, it will be understood that within the broader scope of the present invention are included features and/or components of the same that can be adapted for use in many varied and diverse applications.

In one preferred embodiment of the present invention, the inspection apparatus comprises a housing section and a sensing section, a circuit section, a temperature sensor, and a computer.

The sensing section is mounted to the housing section and is arranged to transmit transmitted ultrasound pulse(s) and receive reflected ultrasound pulse(s), and to provide an analog signal(s) representative of a reflected waveform(s) of the reflected ultrasound pulse(s). The sensing section further comprises a transducer assembly with a transducer placement location.

The circuit section is arranged to generate electric pulse(s) for the sensing section, receive the analog signal(s) from the sensing section and to convert the analog signal(s) to digital signal(s) representative of the waveform(s) of the reflected ultrasonic pulse(s).

The temperature sensor is arranged to ascertain temperature of the quantity of material in the chamber of the container and provide a temperature output. This temperature output would normally be an analog signal which would then be converted to a digital signal.

The computer is arranged to receive the digital signal(s) and said temperature output, and to correlate these with travel distance and time of travel of the transmitted pulse(s) so that with the transmitted pulse(s) and reflected pulse(s) traveling in the chamber of the container, information of velocity of the pulse(s) is able to be developed and related to identification of material and/or objects in the container.

In the presently disclosed embodiment, the transducer assembly comprises at least two transducers, namely a first high frequency transducer and second a low frequency transducer which are better able to transmit pulse(s) in the higher frequency range and in the lower frequency range, respectively. Further, the sensing section is arranged so that either transducer can be mounted in the placement location of the transducer assembly to transmit ultrasound pulse(s).

The preferred configuration of the housing has an overall configuration of a pistol, and comprises an upper horizontally extending upper housing portion having a front end and rear end. The sensing section is located at the forward end of the upper housing portion and the circuit section is located at a rear portion of the upper housing section. The housing further comprises a hand grip portion having an upper end connecting to the upper housing section and a lower end. There is a trigger section mounted to the hand grip portion so as to be operable by a person grasping the hand grip portion. In the preferred form, the upper end of the hand grip portion is located forwardly of the rear end of the upper housing and rearwardly of the front end of the upper housing. The hand grip portion has a lengthwise alignment axis which extends downwardly from the upper housing portion at a moderate downward and rearward slant from a forward to rear lengthwise axis of the upper housing section.

In a preferred form, the upper horizontally extending housing portion has an upper surface portion configured as a mounting platform in which the computer can be positioned. Desirably, the computer has an upper graphic interface which is readily observable by an operator who is grasping the hand grip portion of the housing. The mounting platform to support the computer is positioned along an upper rear surface portion of the upper housing section.

Also, there is a power supply section that is connected to a lower end portion of the hand grip portion of the housing. The power supply section is preferably removably mounted to the hand grip portion. The power supply section may be battery-powered for manual applications, or may be electrically powered for use in such applications as real-time process monitoring and control. The person of ordinary skill in the art will understand that the instant invention as embodied herein may be configured so as to be integrable with other system and/or process components for an intended application.

The temperature sensor has a desired location at the forward end portion of the sensing section so as to be in close proximity to the transducer that is located in the placement location. Thus, with the transducer being positioned with a contact surface thereof in contact with a container to be inspected, the temperature sensor is also adjacent to the container.

Each of the transducers is part of a related transducer unit, with each transducer unit comprising a holding case in which the related transducer is positioned and an electrically connecting portion enabling the transducer to have an operative connection with the circuit section with the transducer being in placement position. Each of the transducer units is removably mounted in the placement location so that each transducer as part of its related unit is removed from and replaced in the sensing section as a transducer unit.

The sensing section comprises a transducer unit engaging portion adapted to engage a rear portion of the transducer unit which is in the placement location. The engaging portion has a compression spring which yieldingly engages the transducer unit to urge it to a forward engaging position. There are least two temperature sensors, with each of the two temperature sensors being a component of the related one of the transducer units and positioned so as to be located at a front forward contact base of its related transducer so as to be able to be in close proximity with a container being inspected by the inspection apparatus. Each of the transducers comprises a front contact surface arranged to be positioned and adjacent to a surface of the container being inspected, and a front contact layer of synthetic rubber and/or other material which covers said front contact surface. The synthetic rubber and/or other material is moderately yielding so as to be able to conform to the surface of the center being inspected. The front contact layer is bonded to the contact surface of its related transducer by means of an liquid adhesive which is applied between the contact surface of its related transducer and the front contact layer, with the front contact layer being pressed against the adhesive layer in order to (be exposed to a low pressure environment to) cause degassing and bonding of the adhesive layer. The liquid adhesive layer in a preferred form comprises at least in part urethane.

The circuit section comprises a pulser section which in turn has a high frequency pulser circuit portion arranged to receive a high freqency trigger signal and a low frequency pulser circuit portion arranged to receive a lower frequency trigger signal. The high frequency pulser circuit portion is arranged to receive the high frequency signal, which is directed to a driver circuit which sends a gate signal to a high voltage switch which outputs a high voltage burst which in turn is directed to the high frequency transducer. In the preferred form, the high frequency pulse is a square wave pulse and the low frequency pulse comprises a sinusoidal tone burst or multi-cycle tone burst sine wave.

The circuit section comprises a receiver circuit section which is arranged to receive the analog signal(s) from the sensing section. The receiver circuit section also comprises a voltage limiter to limit voltage of the received signal(s) to an acceptable level. The receiver circuit also includes a preamplifier to boost the received signal(s) to an intermediate level so that the signal may be further processed without appreciable degradation of the signal-to-noise ratio. Also included is a high-pass filter to pass higher frequency portions of the received signal pulse(s). The receiver circuit section also comprises a variable gain amplifier to modify amplitude of low-level signal(s). The variable gain amplifier is under the control of the circuit section and also under control of a user of the inspection apparatus by inputs entered through the computer. The receiver circuit section further comprises a post-gain amplifier that allows dynamic control of signal sensitivity and input linearity with a minimum noise figure.

The circuit section further comprises a signal processing and control section which is arranged to receive the analog signal(s), convert the analog signal(s) to digital signal(s), and to select an adequately large number of samples from the digital signal(s) representive of a received waveform(s) of a reflected sound pulse(s), which are then transmitted to the computer. The signal processing and control section also functions to send enabling signal(s) through the pulser section to initiate low frequency and high frequency pulse(s).

Another function of the signal processing and control section is to control delay time, digitizing rate, frequency pulse width, burst frequency, and combinations of the same, and of electric pulses being transmitted to the transducers.

The signal processing and control section further comprises a microprocessor having operative connections through the computer section to control delay time, digitizing rate, frequency pulse width, burst frequency, electric pulses, and combinations of the same; these may be controlled through instructions from the computer, which instructions are capable of being operator entered.

The signal processing and control section further comprises a programmable gate array component having an operative connection with a waveform analog-to-digital converter that effects waveform or signal control functions, including those recited immediately above.

Yet another function of the signal processing and control section is to receive analog temperature outputs from the temperature sensor and to transmit the temperature outputs as a digital signal to the computer section. Further, the signal processing and control section is responsive to interrogation from the computer whereby an operator utilizing the computer is able to ascertain from the signal processing and control section the various temperature readings. The computer is also configured to periodically input temperature readings received from the signal processing and control section. The signal processing and control section is also responsive to interrogation from an operator utilizing the computer to ascertain temperature readings from the signal processing and control section. The computer is also arranged to periodically request and receive these input temperature readings from the signal processing and control section to the computer.

The circuit section further comprises a RAM component having an operative connection to the computer section and also to a microcontroller of the circuit section so as to be accessible to an operator utilizing the computer section. The RAM component comprises unique address lines and data lines for directing data and information to and from the appropriate locations in the circuit section of the inspection apparatus. Thus, the RAM circuit enables the operator of the apparatus to obtain and temporarily store useful operation information, including diagnostic data, and/or additional data analysis information resulting from an interrogation of a container. For example, an operator may store material identification results, as well as audio and visual indicators (e.g., fill-level information, detection of contraband, detection of hidden compartments, and anomalies within the container or bulk solid) by which an operator can make a rapid determination regarding the state of the cargo or item being inspected.

The circuit section further comprises a FIFO component having an operative connection to the computer section and also to the microcontroller of the circuit section so as to be accessible to an operator utilizing the computer section. The FIFO component stores ultrasound waveform data received by, and digitized within, the inspection apparatus. The FIFO component comprises data lines for directing data and information to and from the appropriate locations in the circuit section of the inspection apparatus. For example, the FIFO can store waveform data related to material identification by which an operator can determine the materials found within a cargo container or item being inspected. Waveform data retrieved from the FIFO component are transmitted to the computer for further analysis and/or determination.

The inspection apparatus further comprises a display section to provide visual indicators of, and/or auditory prompts for, at least one of the following: activation of the apparatus, power to the apparatus, component disconnects, low battery, and errors encountered during operation of the inspection apparatus.

Further, the circuit section comprises a storage component operatively connected to a microcontroller of the circuit section in order to retain configuration and setting information when power is lost or shut off to the apparatus. Thus, when an operator starts operation of the inspection apparatus, the same operating parameters will be extant as at the time of shut down. In a preferred form, this storage component comprises an EEPROM storage component.

The circuit section is arranged so that in addition to receiving the analog signal(s) and converting them to a digital signal(s), the the average amplitude of the digital signal(s) is computed by the computer to establish a baseline waveform(s). The baseline waveform is the zero or basis point from which further waveform or amplitude computations can be made. The circuit is further arranged so that an adequate number of samples are likely to be transmitted to the computer. The computer then identifies and establishes a noise-level amplitude, a threshold amplitude below which a pre-selected percentage of incoming sample amplitudes will fall; these signals are not recognized as being significant.

The computer is further arranged to select a threshold level of signal amplitude which is a predetermined amplitude greater than the noise level amplitude by which peaks of a particular waveform(s) are identified. The threshold amplitude also serves as the basis upon which further amplitude calculations may be based. For example, if the incoming signal is above the amplitude threshold and above the noise threshold, the computer uses the echo pulse in its material determination calculations.

The computer is also arranged to select peaks in the waveform in order to ascertain time intervals and paths of travel (e.g., time-of-flight data) for waveform peak portions that are above the threshold level. For example, a time interval between a first back wall echo and second back wall echo represented in the waveform(s). In an occurrence where a second back wall echo is not able to be identified, the computer is arranged to then ascertain location of a leading edge of the first back wall echo in the waveform(s)

for ascertaining a time interval between a forward ringdown portion of the waveform and the leading edge portion of the first back wall echo of the waveform.

Further, the computer is arranged to ascertain amplitude peak portions of the waveform(s) and to ascertain an early arriving peak waveform portion(s) of lesser amplitude than a later arriving waveform(s) for identifying false echo(es) in the waveform(s) representing the presence of a reflected interface other than a back wall interface.

In making a comparison between the first and second back wall echo portions of the waveform(s), the computer is arranged to utilize a correlation technique to correlate the first and second back wall echoes as a means of ascertaining a time interval between the first and second back wall echoes.

The computer is also arranged to establish a threshold level of received waveform(s) to identify the time interval(s) between waveform peaks and also a temperature input from the temperature sensor, as well as the travel time input, corresponding to said time interval(s) and travel distance input to establish a temperature adjusted velocity of ultrasonic pulses.

The computer has a database with a listing of materials and their associated ultrasonic property values of materials (including acoustic velocity, attenuation, etc.), as well as the related temperature-adjusted ultrasound velocity values for those same materials, as the computer is configured to correlate the temperature adjusted velocity values of the ultrasonic pulse(s) to identify the material through which the ultrasonic pulse(s) has travelled.

The computer also comprises a user input interface by which at least one of amplitude, burst frequency, pulse width, digitizing rate, and combinations thereof are able to be controlled by the user. Further, the computer desirably comprises a graphic display by which the waveform(s) is physically displayed to the user. Also, the computer has the capability of displaying parameters of the received waveform comprising at least one threshold level(s), noise level(s), waveform portion locations relative to waveform analysis and/or examination, and combinations thereof.

In the method of the present invention, an ultrasound inspection apparatus is provided as described above. In this method, there is a selected front wall transmitting location at which the ultrasound pulse is to be transmitted to the back wall receiving location. The travel distance is then ascertained from the front wall to the back wall receiving location, and information related to this travel distance is entered into the computer either remotely, manually, or by transmission. The inspection apparatus is positioned so that a front contact portion of the transducer is positioned at the transmitting location on the container and an ultrasound pulse is transmitted into the container toward the back wall receiving location and a reflected pulse is received from the back wall.

An analog signal is developed from the received echo pulse and transmitted to the circuit board section where the analog signal is converted to a digital waveform, which in turn is transmitted to the computer.

The temperature sensor is utilized to ascertain temperature of the material in the container and to transfer or transmit information related to said temperature to the computer.

The computer is caused to correlate travel distance of the ultrasound pulse(s), time of travel of the pulse(s), and temperature of the contained material, to develop a temperature-corrected velocity value of the ultrasound pulse(s), and to correlate information relating to various materials that could be in the container and then to develop information as to the contents of the container and/or to ascertain the presence of an object in the container.

Other features of the present invention are apparent from the following detailed description.

BRIEF DESCRIPTION OF THE DRAWINGS

FIG. 4d is a top view of the transducer assembly;

FIG. 5a is an exploded view of several components of the sensor receptacle assembly;

FIGS. 5b, and 5c are isometric drawings showing some of the components of FIG. 5a assembled, these being taken from different views;

DESCRIPTION OF THE PREFERRED EMBODIMENT

A better understanding of the present invention will be obtained by providing an overview in which the main components of the system are described, followed by a more general description of the operation of the same. After that, the various components and method of the present invention will be described in more detail.

a) Introduction

The apparatus 10 of the present invention can be considered as comprising two main components, namely an inspection assembly 12 and a host computer 14. Since the presently preferred configuration of the inspection assembly 12 is in the form of a hand held gun or pistol for convenience, the inspection assembly 12 will commonly be called the "gun assembly" 12, or the "gun" 12. Also, a preferred form of the computer 14 for portable and/or manual mode applications of the present invention is at present a Personal Digital Assistant (PDA). For automated applications such as for system monitoring and control, the computer 14 may also be of a desktop or laptop configuration. Thus, the terms "inspection assembly" 12 and "computer" 14 are not limited to any one particular configuration or item type. Further, within the broader scope of the invention, these terms are intended to cover other configurations able to perform the main functions of these components for the intended purpose or application.

Figure 1:
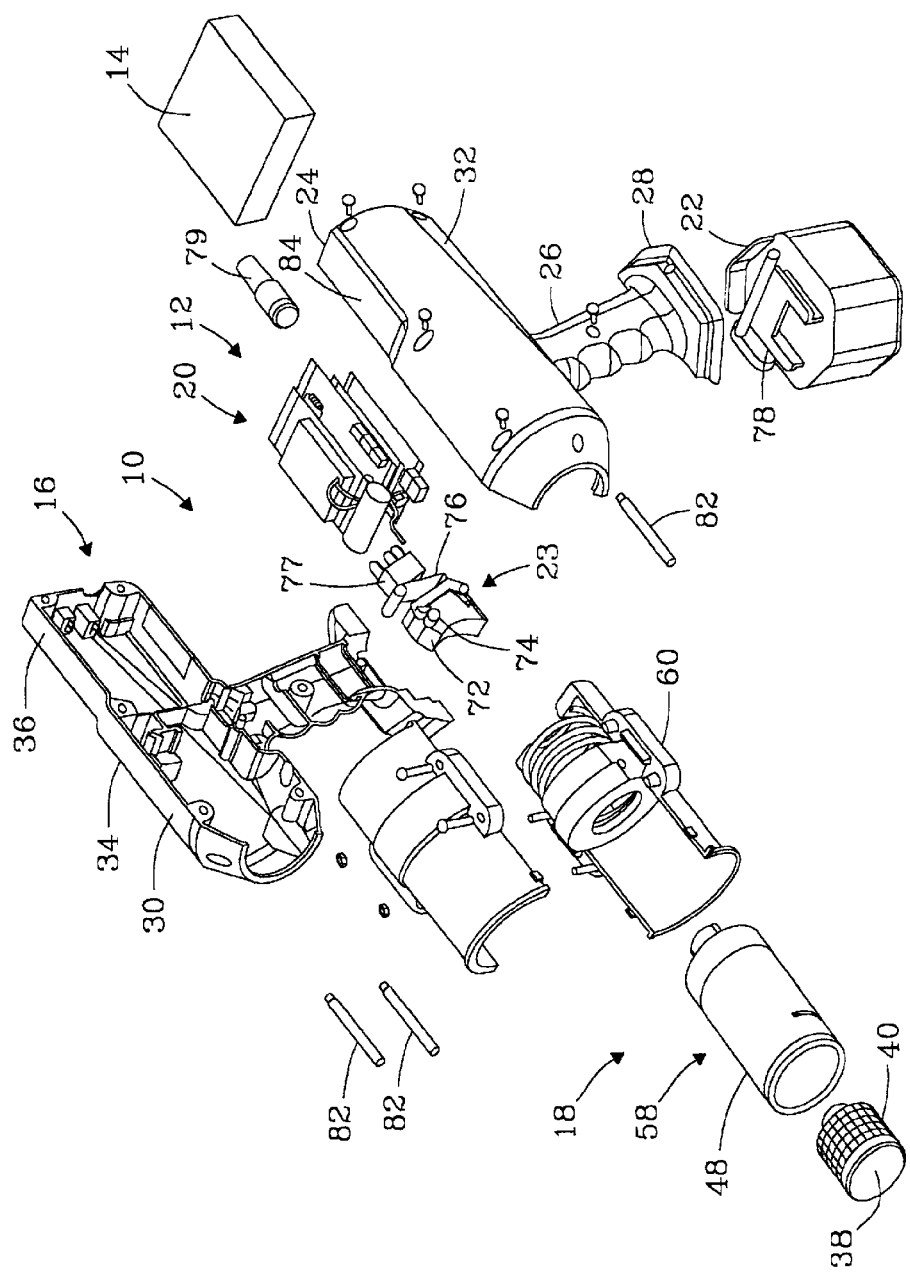
FIG. 1 is an exploded isometric view of the apparatus of the present invention.
Figure 2:
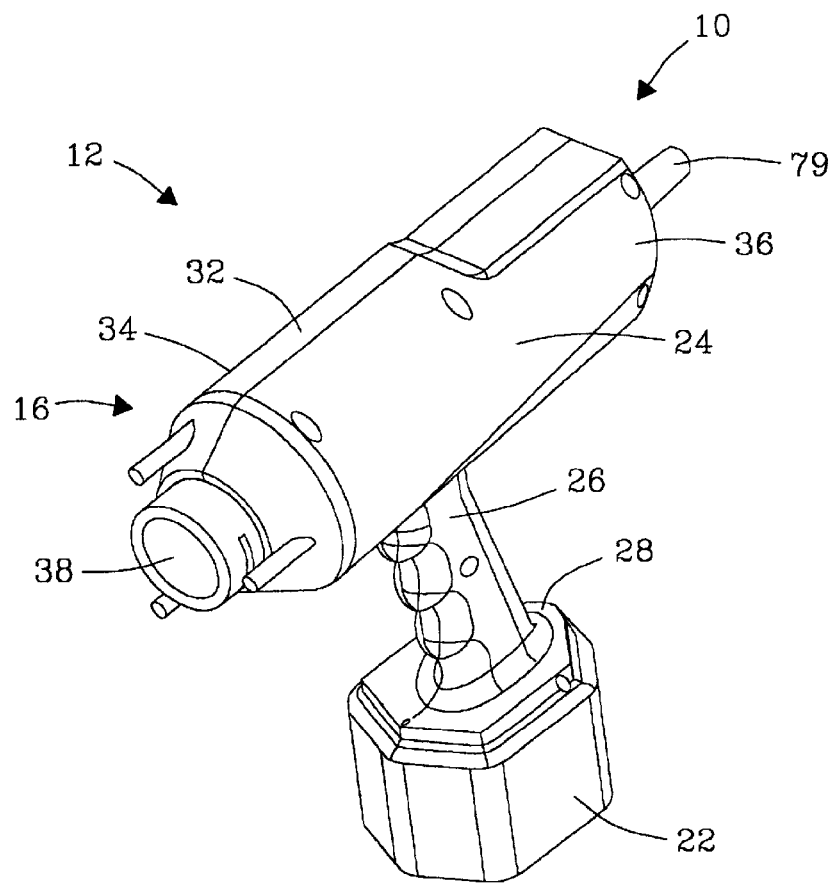
FIG. 2 is an isometric view of the inspection gun assembly of the present invention.

Reference is first made to FIGS. 1 and 2, with FIG. 1 being an exploded view of the main components of the gun assembly 12, and FIG. 2 being an isometric view of the gun assembly 12 assembled in its operating condition.

The gun assembly 12 comprises a section housing 16, a sensing section 18, a circuit section 20 (hereinafter called the "circuit board section" 20), a power supply 22, and a trigger assembly 23. These components (18–23) are mounted to (or mounted in) the gun housing 16.

The gun housing 16 comprises an upper housing section 24 having overall a generally elongate cylindrical configuration, and a handle portion 26. The handle portion 26 is connected to the upper housing section 24 in a manner that the gun assembly 12 has the overall configuration of a pistol, so that with the upper housing section 24 being horizontally aligned, the handle portion 26 is connected by its upper end portion to the upper housing section 24 at a middle section thereof, with the handle portion extending downwardly from the upper housing section 24 with a moderate downward and rearward slant. In this text, the handle portion 26 will often be referred to as the "pistol grip" or "hand grip". The inspection gun assembly 12 is light-weight and well-balanced so that it is easy to handle. At the lower end of the pistol grip 26, there is a mounting structure 28 by which the power supply 22 is mounted to the gun assembly 12. The power supply 22 may be powered electrically or by battery. When the instant invention is configured for use in the manual mode, the power supply 22 is preferably a 12-volt battery.

In order to describe the orientation and relative location of the various components, the gun assembly 12 will be considered as being positioned so that the upper housing section 24 is considered to be horizontally aligned, and has a horizontal alignment axis with the forward end being at one end of the alignment axis and the rear end at the other. Thus, the terms "forward", "rear", "upperward", "downward", "lateral", and other terms corresponding with the same will be with reference to the term "horizontal" assuming that the gun assembly 12 is positioned with its upper housing portion horizontally aligned. It is to be understood of course in various modes of operation, the gun assembly 12 may be in different positions than being "horizontally aligned".

Also the term "front wall" is to be interpreted to mean a wall portion, panel, or other surface position at which the inspection apparatus is first positioned or located to transmit the ultrasound pulse into a container, and the term "back wall" is to be interpreted as a second wall portion, panel, or surface which is at a location where the ultrasound pulse from the front wall is reflected back to the front wall. Thus, the "front wall" and "back wall" are not intended to necessarily mean locations on a container which in the traditional sense might be considered the "front or back" of the container.

It can be seen that the housing section 16 is made in two halves 30 and 32 which are separated along a vertically aligned, longitudinally extending center plane. The upper housing section 24 can be considered as having a forward housing portion 34 and a rear-housing portion 36. The sensing section 18 is positioned in the forward housing portion 34, and the circuit board section 20 is located in the rear-housing portion 36.

The apparatus 10 of the present invention is particularly adapted to be used for non-invasive and non-intrusive interrogation of a variety containers, including sealed and unsealed containers, flow and process-control systems, shipping containers, cargo holds, and bulk material carriers, etc., as well as the materials contained therein. One practical application of the present invention is to examine liquid-filled containers. Thus, in much of the following description, the operation of the present invention will be described in an environment where the apparatus is being used in inspecting a liquid-filled container, either a smaller container (e.g. a 55-gallon drum or a yet smaller container) or a larger container such as a large tank structure containing a liquid material, such as that carried on a tanker trailer or a tanker truck, which structure may be 8 or 9 feet in diameter. It will be understood by those of ordinary skill in the art that in the broader scope, the invention is not limited to interrogation or investigation of liquid material containers only, but can be used to inspect, or interrogate non-liquid material containers, including bulk-solid form commodities as well as bulk solid-filled containers.

To describe now briefly the method of the present invention, the inspection of the container is initiated by the user positioning the gun assembly 12 against the container to be inspected by placing the front-end surface 38 of a transducer 40 of the sensing section 18 against the surface of the container being inspected. The trigger of the trigger assembly 23 is squeezed to activate the apparatus and to transmit an ultrasound pulse through the container wall and into the containing chamber of the container. (In the following text, the term "pulse" should be interpreted to include a single pulse, a "burst" comprising a series of pulses, a section of a sine wave, etc.).

The ultrasonic pulse emitted from the front surface 38 of the transducer 40 in the gun assembly 12 travels through the material in the container being inspected. When the ultrasonic pulse reaches the far wall of the container, it is reflected back as an acoustic echo to the transmission location. The acoustic echo reaches the transducer 40, which receives this acoustic echo and translates the acoustic echo into an analog electrical signal. The analog signal is then sent into the circuit board section 20 for further processing to translate the analog signal into a digital signal. The digital signal is then transmitted from the circuit board section 20 to the computer (e.g., PDA, laptop, desktop, or other computer) 14, where various functions are performed. A primary function of the computer 14 is to compare information received from the digital waveform to various reference data held in a database of the computer 14 to see if the received waveform information matches the reference waveform information for a particular material expected to be present in the container.

In the present preferred embodiment, the computer 14 analyzes the difference in time (also called "delta time") from the transmission of the pulse to the receiving of the echo, and this difference in time is correlated with the distance of the ultrasonic pulse and the temperature of the material through which the ultrasonic pulse travels. Within the broader scope of the present invention, other characteristics of the waveform can be analyzed and compared with reference waveforms, including amplitude, phase shifts, frequencies, relationships between the various aspects of the waveform, or combinations thereof, which aspects represent the unique "fingerprint" of a given waveform, etc.

The computer 14 looks for a proper match-up between the received waveform (and its characteristics) with a database of reference information corresponding to various materials. When a match-up is found, the pertinent information is displayed or otherwise communicated to the user so that appropriate action can be taken. For example, if the analysis of the acoustic echo by an inspection officer in a border control application indicates that there is possibly something improper about the container or its perceived contents, the officer can impound the container. Alternatively, if no match-up occurs (i.e., the inspection/interrogation proves negative), the officer can allow a container to pass inspection. And, within the broader scope of the present invention, the database match-up process applies equally well to interrogation of online and/or real-time monitoring of materials in flow systems (e.g., pipes, duct-work, venting, etc.) or process control stations, as well as inspection of bulk liquids, as well as solid form commodities inside or outside of sealed containers.

As indicated above, temperature must be taken into consideration since the acoustic velocity of a material will vary as a function of temperature. For example, the acoustic velocity of water may increase with higher temperatures, while the acoustic velocity of gasoline may decrease with higher temperatures.

Further, in some applications, there may be an object of interest concealed within the greater bulk material in a container. For example, a hidden package of contraband may be located within a bulk liquid or dry solid commodity, etc. In this instance, the ultrasonic pulse would reach the interface of the object within the bulk-contained material. As the object would be different from the bulk material, an acoustic echo would result at the interface of the object and the material. This early acoustic echo will reach the transducer 40 prior to the time that the first main acoustic echo from the far container wall reaches the transducer 40, permitting the object of interest to be ascertained and identified.

A more specific description of the various components of the apparatus and also the method of the instant invention are now presented.

b) The Sensing Section 18

Two transducers 40 are utilized with the gun assembly 12, a first low-frequency transducer 40, and a second high-frequency transducer 40. The low-frequency transducer 40 operates at 200 KHz. The high-frequency transducer 40 operates at 1 MHz. In general, low-frequency ultrasonic pulses can travel further than high-frequency ultrasonic pulses. Accordingly, the low-frequency transducer 40 is ordinarily used to interrogate or investigate larger containers (i.e., an 8 foot by 9 foot diameter tank on a trailer) and the high-frequency transducer 40 is used for smaller containers (i.e., a 55-gallon drum containing a bulk liquid) unless other attenuation factors must be considered. The particular frequencies chosen are those found to provide the best overall advantageous selection, but obviously more than two transducers could be selected to address the various investigation applications. For example, frequency choices depend on a number of factors, including, but not limited to, the dimensions of the container being examined, the type of material in the container, temperature or other ambient environmental conditions, rheologic and acoustic properties of the material, as well as other factors. Thus, the frequencies selected can be varied depending on the need or application.

Each transducer 40 (low-frequency or high-frequency) is, or may be, of a conventional commercial configuration, but with some adaptations. For example, the low-frequency transducer 40, in its commercial configuration, is somewhat larger in diameter than the high-frequency transducer 40. Accordingly, the casing of the low-frequency transducer 40 has some of the excess material on the outside of the housing machined off so that it has an exterior configuration the same as (or closely matching that of) the high-frequency transducer 40.

As indicated earlier, the transducer 40 has a front-end contact surface 38 that is positioned and pressed against the wall of the container being examined or interrogated. The transducer 40 has some unique features. In the present embodiment, for example, the transducer 40 has a front end contact surface 38 comprising in part a unique dry-coupling membrane that is adhered to the surface, which membrane couples the acoustic transmission through the surface of a container without the need for acoustic gels or other coupling agents. The transducer 40 is thus designed in such a way as to substantially eliminate the need for any contact gel (an "acoustic gel"), which gel is commonly used in the prior art for efficiently directing (coupling) acoustic energy into a material.

Figure 3:
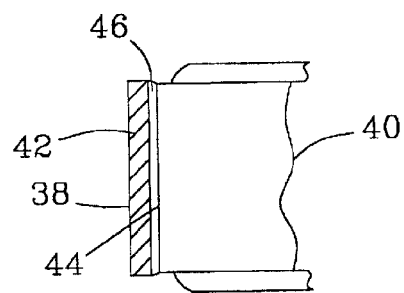
FIG. 3 is a cross-sectional view taken along the longitudinal center line of a forward portion of the transducer of the inspection gun assembly.

Reference is now made to FIG. 3, which illustrates the front-end portion 38 of the transducer 40 in a cross-sectional view taken along a plane coincident with the longitudinal centerline of the gun assembly 12. There is a synthetic rubber or rubber layer 42, which is in the form of a circularly shaped disc, covering the entire front face 44 of the transducer 40. In a preferred embodiment, this layer 42 is a neoprene layer. The layer 42 is bonded to the forward face 44 of the transducer 40 by means of an adhesive layer 46, which in this embodiment is a thin urethane layer 46. The manner in which the neoprene layer 42 is applied is as follows. First, liquid urethane is applied to the back surface of the neoprene layer 42, and also to the front surface 44 of the transducer 40. (Alternatively, it may be adequate to first apply the urethane layer to only one of these two surfaces.) The neoprene layer 42 is then put in place at the front face 44 of the transducer 40, and pressed against the urethane layer 46. A pressure plate is then placed against the neoprene layer 42, and pressed against the neoprene layer 42. The plate is held in position by clamps (e.g. C-clamps) or some other similar device(s). Then, with its pressure plate still clamped against the neoprene surface 38, the transducer 40 is placed in a vacuum (i.e. a low-pressure environment) for about 15 to 20 minutes to allow any trapped air to escape from the semi-liquid urethane layer. The transducer 40 is then taken out of the vacuum environment and allowed to cure at ambient conditions and atmosphere for 24–48 hours, or until the seal is completely and properly cured. The excess urethane squeezed out from under the neoprene layer is then trimmed away from the transducer after curing and solidification.

In a current configuration, the neoprene layer 42 selected is about 0.0625 inches in thickness for the high-frequency transducer, and is about 0.1875 inches thickness for the low-frequency transducer.

The thickness of the neoprene layer 42 can be varied depending upon the intended application. For example, on the low side, the neoprene layer 42 could be as small as 0.06, 0.05, 0.04, or possibly even 0.03 inches. Further, the neoprene layer 42 could be any one of the one-hundredth inch incremented dimensions between 0.8 and 0.16 inches, and beyond, the thickness of 0.16 in one-hundredth inch increments as high as 0.2, 0.3, or 0.4 inches. The choice of thickness would depend upon various processing conditions, but also would vary in accordance with the configuration of the surface of the container being examined. Also, if there were irregularities or reverse curves in the container surface being contacted, the thickness could be changed so as to better conform to these surface configurations.

The neoprene suitable for the present invention should have low acoustic impedance and the following characteristics:

The dry coupling properties of importance for the commercial grade neoprene rubber material used in the preferred embodiment of the present invention include 1) a 40A Durameter (e.g., "soft") material hardness, 2) an acoustic impedance of 2.1 gm cm$^{-2}$ sec$^{-1}$×10$^5$, 3) a longitudinal acoustic velocity of 0.063 inches per microsecond, and 4) a density of 1.31 gm cm$^{-3}$.

Obviously, these parameters can be varied, and may vary as follows:

Material hardness could range on the low side from 40A ("soft") grade through 50A ("medium") grade to 70A ("hard") grade on the high side.

Acoustic impedance could possibly range on the low side from 1.0, 1.5, or 1.8 to a value on the high side from 2.5, 3.0, 3.5, or 4.0 gm cm$^{-2}$ sec$^{-1}$×10$^5$.

Longitudinal acoustic velocity could range from 0.05 on the low side to a value 0.065, 0.07, 0.075, 0.08, or 0.085 inches per microsecond on the high side.

Density (gm cm$^{-3}$) could range from 0.9, 1.0, 1.1, or 1.2 on the low side to 1.35, 1.5, 2.0, 2.5, 3.0, or 3.5 on the high side.

While neoprene has proved to be quite satisfactory as a coupling membrane or layer material 42, other materials could be used for the layer 42. Among the candidates for such materials are: solid water or other aqueous bacteriostatic standoff material, as for example, Aquaflex® (Parker Laboratories, Inc., Fairfield, N.J. 07004, USA), silicone rubber, room temperature vulcanizing (RTV) silicone rubber, butyl rubber, urethane, polyurethane, thermoplastic urethane, Ecothane® and Pellathane® (Optimer, Inc., Wilmington, Del. 19804, USA), etc.

To describe the other components of the sensing section 18, reference is now made to FIGS. 1, 4a–4d, 5, 6, and 7. The transducer 40 is positioned in the forward part of a generally cylindrical holding case 48. A temperature sensor 49, which in this embodiment is a thermistor 49, is located adjacent to the sidewall of the transducer 40, and could be positioned in a slot in the transducer sidewall. Also positioned in the case 48 is a socket member 50 that is connected by a cable 52 to an electrical connector 54. Also at the rear end of the holding case 48, there is a rear-holding member 56 having an annular configuration and engaging the connector 54.

Figure 4A:
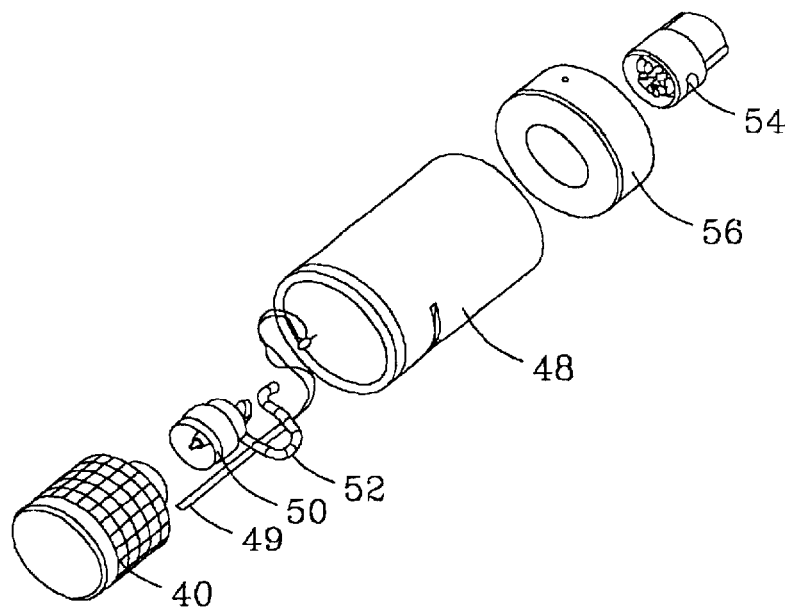
FIG. 4a is an exploded view of the transducer assembly of the present invention.
Figure 4B:
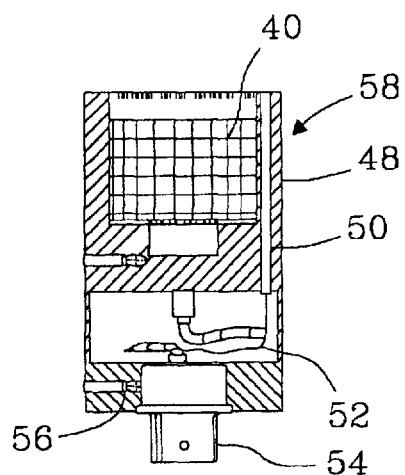
FIG. 4b is a sectional view taken along the center line of the transducer assembly.
Figure 4C:
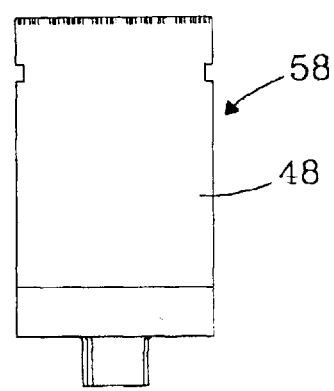
FIG. 4c is a side elevational view of the transducer assembly.
Figure 6:
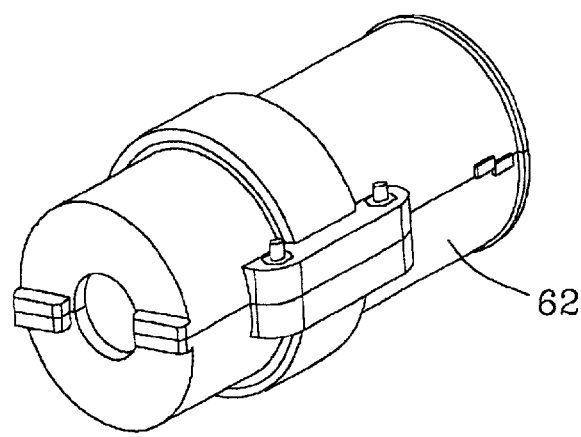
FIG. 6 is an isometric view of the receptacle housing of the sensor section.
Figure 7:
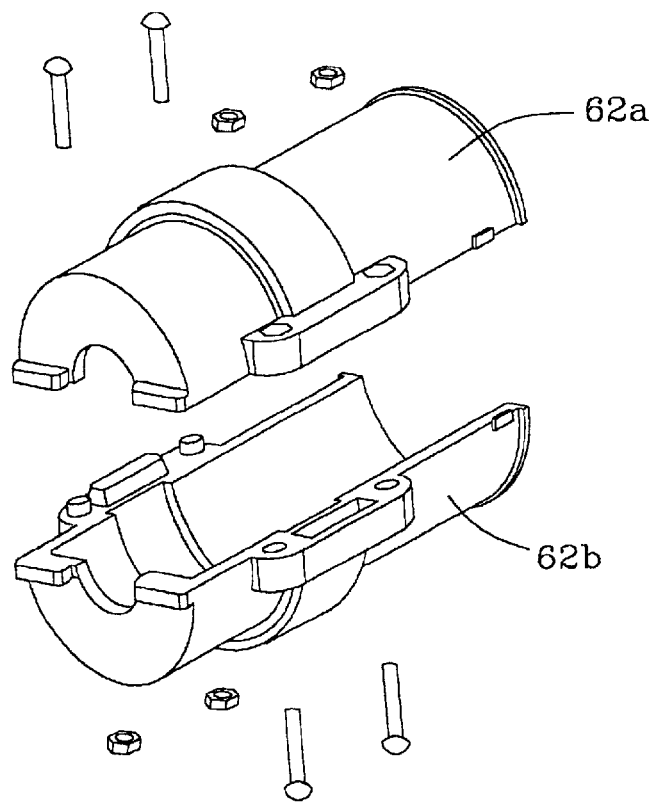
FIG. 7 is an isometric view similar to FIG. 6, but showing the two halves of the receptacle housing apart from each other.

The transducer 40, the socket 50, the cable 52, the connector 54, the holder member 56, the temperature sensor 49, and the holding case 48 function as one unit, which unit is mounted in the forward end portion 34 of the upper housing section 24. These components 40, 48–49, and 50–56 are collectively referred to as the "transducer assembly 58" or as the "transducer unit 58". FIG. 4a shows the transducer assembly 58 in exploded component view. FIG. 4b shows the transducer assembly 58 in cross-section, taken along a longitudinal plane extending through the center axis of the transducer assembly 58. FIG. 4c shows the transducer assembly 58 in side-elevational view, and FIG. 4d shows the transducer 58 in top view.

Reference is now made to FIGS. 1, 5a, 5b, 5c, 6, and 7, which show the sensor receptacle assembly 60 in which the transducer assembly unit 58 is mounted for spring-loaded limited back-and-forth movement, and also urged to a forward position. This sensor receptacle assembly 60 comprises a sensor receptacle housing 62 (See FIGS. 6 and 7) that is made in two half sections 62a and 62b split from one another along the longitudinal horizontal center plane. The sensor receptacle housing 62 has a generally cylindrical configuration, and the two half sections 62a and 62b are fastened together by suitable fasteners (e.g. screws) or other means.

Reference is now made to FIGS. 5A, 5B, and 5C which show a portion of the sensor receptacle assembly 60. There is an end-mounting piece 64 which is mounted in the back side of the sensor receptacle housing 62 and an electrical connector 66 which is mounted by its rear-end portion in the end mounting piece 64. A coiled compression spring 68 is mounted in the rear part of the sensor receptacle housing 60 to bear against the end-mounting piece 64 and to press against the transducer assembly 58 and urge it toward a forward position. A suitable tongue-and-slot interconnection is made between the transducer assembly 58 and the sensor receptacle housing 62 as a guide for the back-and-forth movement and also to limit this back and forth movement.

The trigger assembly 23 (FIG. 1) comprises a trigger member 72 (or trigger 72) pivotally mounted about a pivot location 74, a spring member 76 positioned behind the trigger member 72 to urge the trigger member 72 forward, and a trigger switch 77 behind the trigger 72 that connects to the circuit board section 20.

With further reference to FIG. 1, it can be seen that the power supply 22 has suitable mounting components 78 on its top surface which interfit with matching components in the power-mounting portion 28 at the lower end of the pistol grip 26. For example, the connection could be in the form of a slide connection where a battery (i.e., power supply) 22 is positioned behind the lower end of the pistol grip 26 and moved forwardly in sliding engagement with the lower connecting portion of the pistol grip 26.

Also in FIG. 1, a cable connection 79 is shown which connects the circuit board section 20 through a cable (not shown) to the computer 14 to transmit information to and from the computer 14. In one embodiment of the present invention, a cable connection 79 connects the circuit board section 20 to a PDA 14.

In another embodiment of the present invention, a cable connection 79 connects the circuit board section 20 to a desktop computer 14. Alternatively, the output signals from the circuit board 20 could be transmitted by radio-frequency or other carrier wave technologies (e.g., infrared, microwave) to the computer 14.

Also in FIG. 1, three standoffs 82 are shown arranged in a triangular configuration and extending forwardly from the forward end of the upper housing section 24. These can be used to enable the user to position the apparatus 12 in the proper orientation with the adjacent container surface. The current design contemplated by the applicants does not incorporate these standoffs 82. Nevertheless, for some applications, these standoffs 82 could be advantageous for improving coupling of the ultrasound sensor to a surface, whether even, uneven, or contoured.

It will be noted in FIG. 1 that the rear upper surface portion of the gun housing 16 has a flattened surface portion 84 (i.e. a platform 84). This surface portion 84 is provided so that the PDA 14 could be placed on this flat surface or platform and secured in a suitable manner (e.g., Velcro®) or some other fastener or device). Thus, in this manner, the operator could operate the inspector gun assembly 12 while at the same time having the display panel of the PDA 14 in view so that certain readings and information could be displayed or user commands could be input into the PDA 14. Alternatively, the gun assembly 12 could be operated remotely or at a distance from the display computer 14 such that readings, data, and information could be read or user commands could be input from process-monitoring stations or similar flow system applications via radio frequency, ultrasound, and/or infrared signals, or other signaling means.

It is believed that the manner in which the components are assembled is readily understandable from viewing the exploded view of FIG. 1.

c) The Circuit Section (i.e. Circuit Board Section) 20.

The circuit board section 20 comprises four individual circuit board components, namely:
  i. the pulser board 800;
  ii. the receiver board 900;
  iii. signal processing and control board (hereinafter called the "digital board") 1000;
  iv. the communication interface board (hereinafter called the "PicoWeb™ board") 1100.

These will each be described briefly, and thereafter will be followed by a more detailed description.

Figure 8:
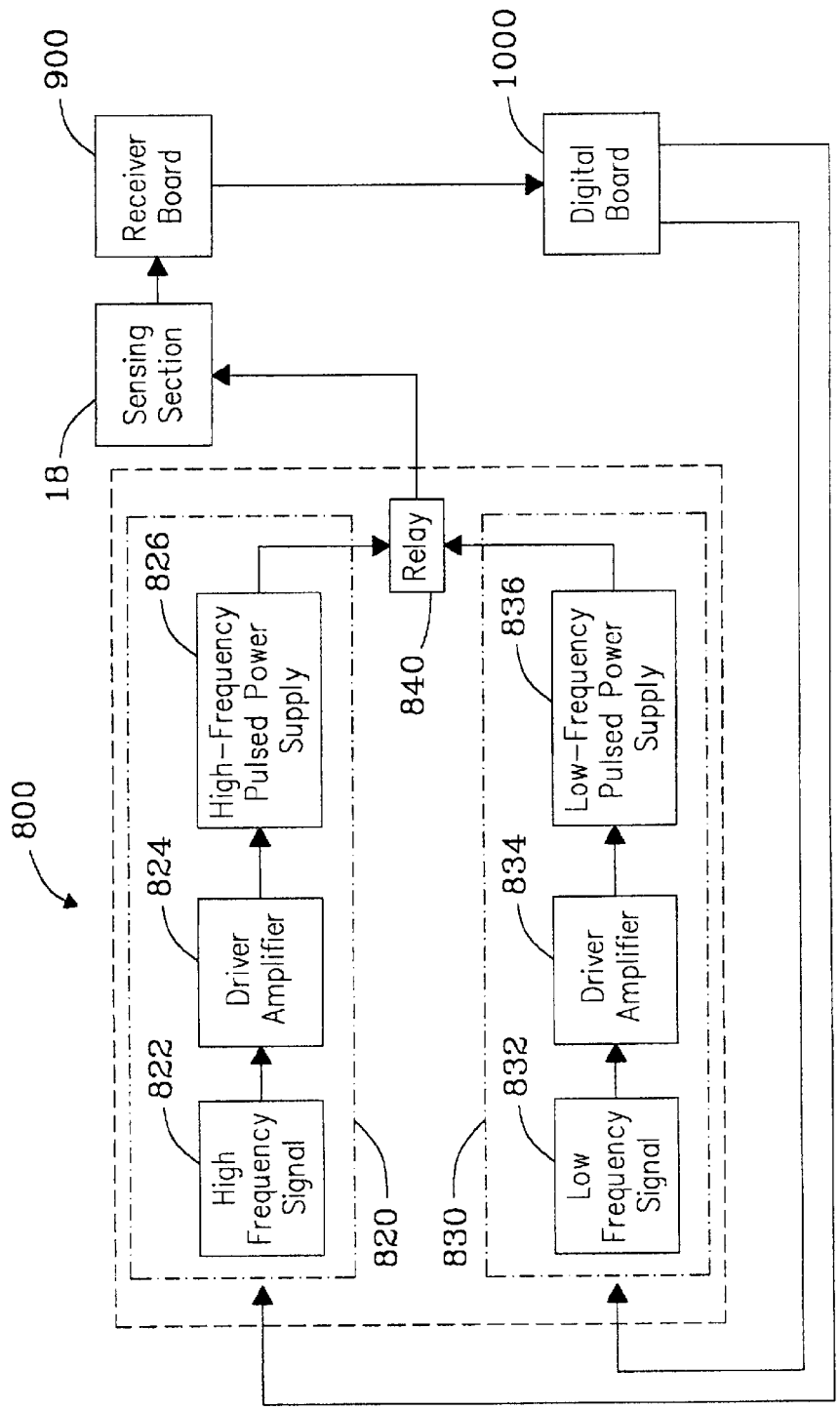
FIG. 8 is a block diagram of the pulser board of the circuit board section.

As shown in FIG. 8, the pulser board 800 has a high-frequency circuit portion 820 and a low-frequency circuit portion 830 that delivers either a high-frequency (HF) pulse or a lower frequency (LF) pulse to the sensing section 18 for interrogation of a container. Depending on which transducer assembly (high- or low-frequency) 58 is positioned in the gun assembly 12, a sync signal is sent via the digital board 1000 to either the high-frequency (HF) circuit section 820 or low-frequency (LF) circuit section 830, thereby readying the appropriate circuit. Then, the pulser board 800 sends a signal to the transducer 40 initiating the appropriate ultrasonic pulse (high- or low-frequency) in the HF circuit 820 or LF circuit 830. The signal generated in either the HF circuit 820 or LF circuit 830 for interrogation of a sample container is routed by means of a relay circuit element 840 on the Pulser Board 800 to the sensing section 18, where it is received by the Receiver Board 900 and sent or transmitted to the digital board 1000 for further processing.

Figure 9:
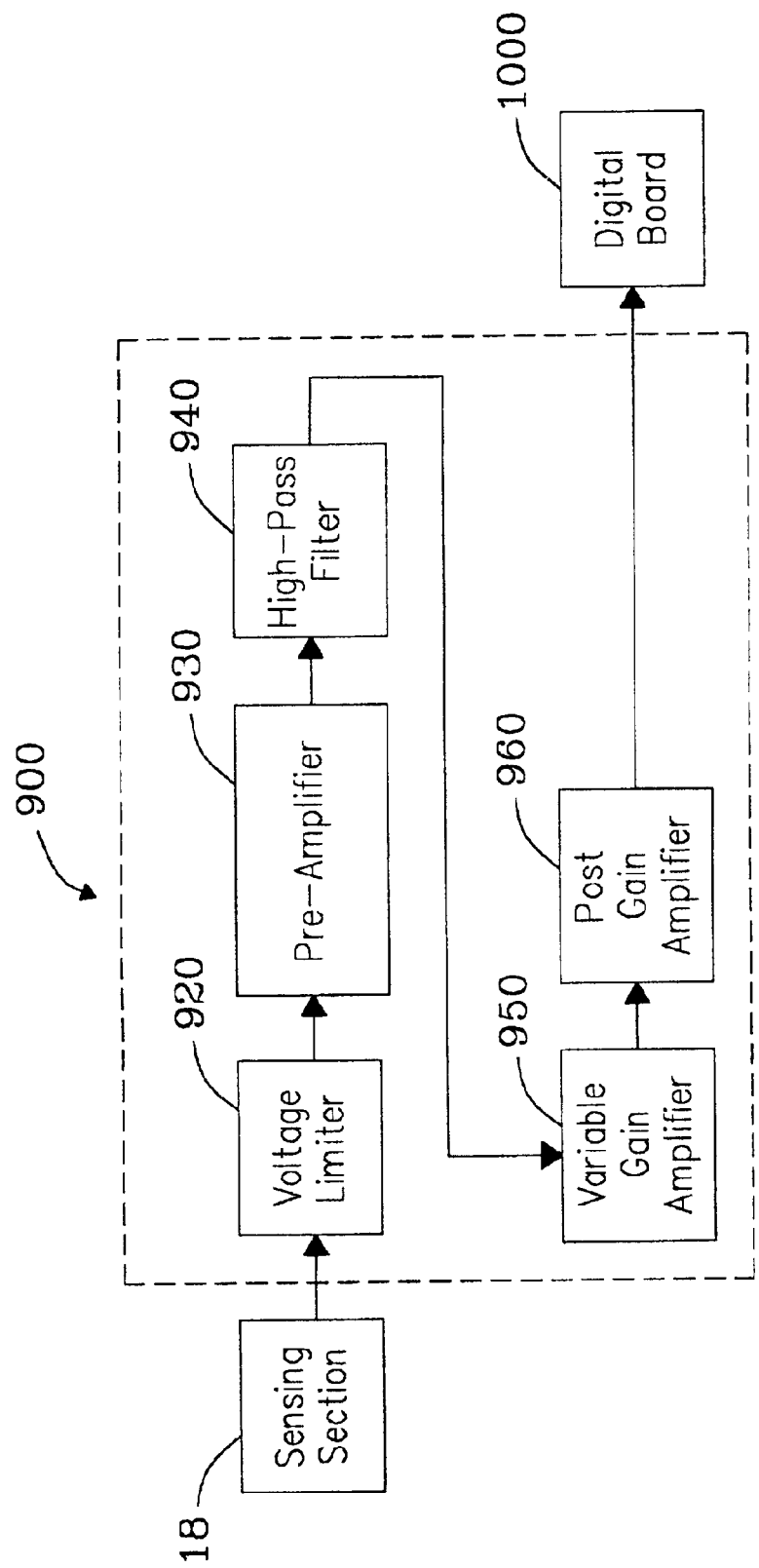
FIG. 9 is a block diagram of the components of the receiver board of the circuit board section.
Figure 10:
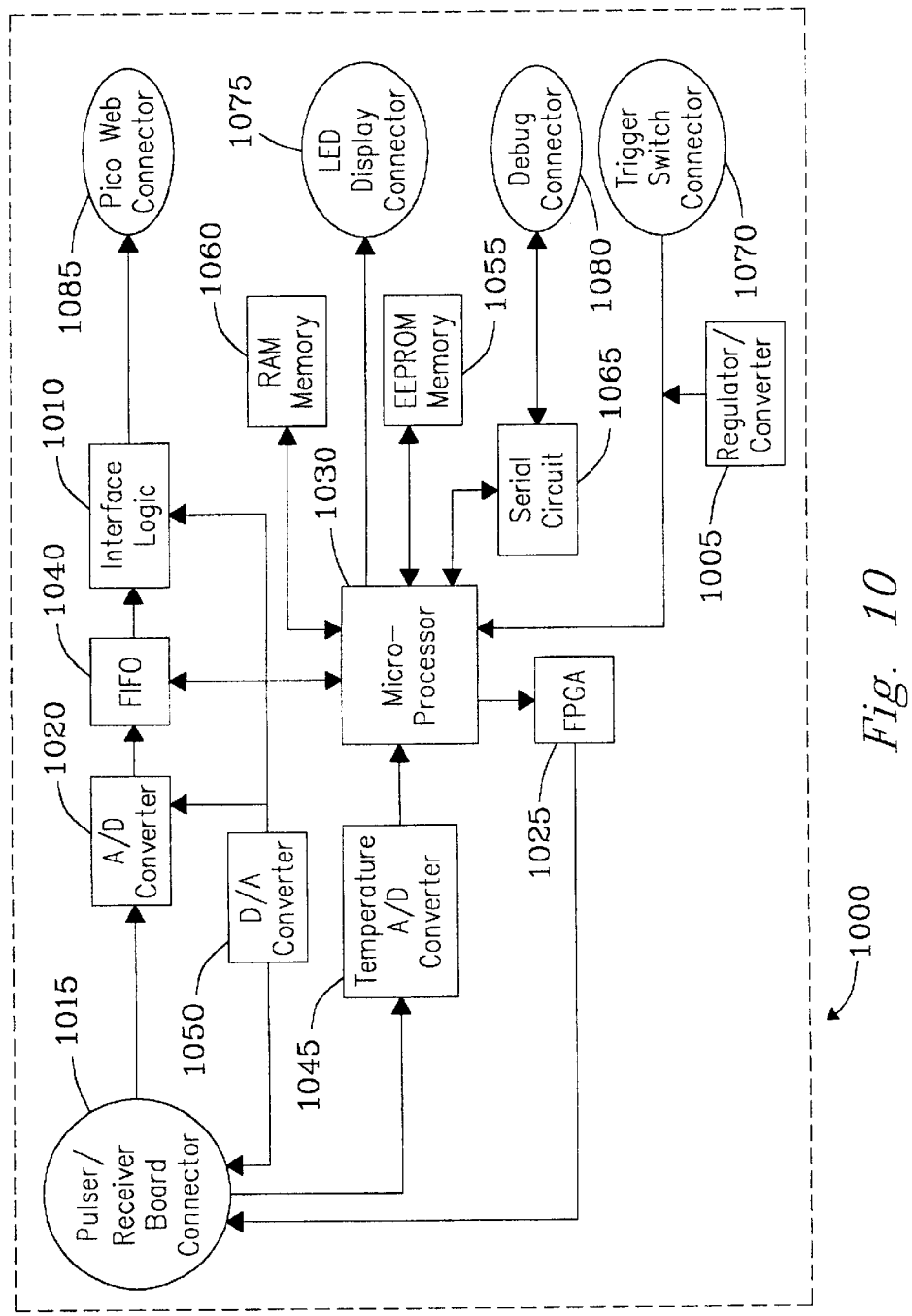
FIG. 10 is a block diagram of the digital board of the circuit board section.

After the transducer 40 receives the acoustic echo or echoes resulting from the interrogation, the receiver board 900 (See FIG. 9) receives the return analog signal from either the high-frequency or low-frequency transducer 40 (depending on the transducer used in the apparatus at that time), amplifies the signal, and then delivers the analog signal to the digital board 1000 (FIG. 10).

The signal processing and control board 1000 (FIG. 10), hereinafter called the "digital board" 1000, performs a number of functions, including the primary function of receiving the analog signal from the receiver board 900, converting the analog signal to a digital signal, and then transmitting the digital signal through the interface board 1100 to the computer 14. The digital board 1000 has a number of other functions which will be described more fully later herein.

The interface board 1100 functions as a communication link between the digital board 1000 and the computer 14, placing the information from the digital board 1000 in a format which can be readily received by the computer 14. The interface board 1100 also acts as a communication link between the computer 14 and digital board 1000 to send information to and from the computer 14 to the digital board 1000.

The interface board 1100 may be of a conventional or commercially available type. In the preferred embodiment, the interface board is currently a PicoWeb™ Ethernet server communication board (Lightner Engineering, La Jolla, Calif. 92037-3044, USA).

At this point, these four boards will be described in more detail.

i. The Pulser Board 800.

Reference is made to the block diagram in FIG. 8, which illustrates and describes the pulser board 800 circuit in more detail.

The initial input to the pulser board 800 comes as a trigger, or sync, signal through the digital board 1000 (FIG. 10), as the switch assembly 23 is activated from the action of the operator (i.e. user) squeezing the trigger 72 to activate the trigger switch 77.

It can be seen in FIG. 8 that there are two pulser sections, namely the high-frequency pulser section 820 (comprising path elements 822–826) and the low-frequency pulser section 830 (comprising path elements 832–836). The signal is either a high-frequency "activating" signal 822 or a low-frequency "activating" signal 832, depending on whether the high-frequency or low-frequency transducer 40 is mounted in the gun assembly 12. The initial signal is directed to and through the high-frequency pulser section 820 if it is a high-frequency signal 822. The initial signal is directed to and through the low-frequency pulser section 830 if it is a low-frequency signal 832.

When the high-frequency activating signal 822 is received from the digital board 1000, it is directed to the driver amplifier circuit 824, which then sends a gate signal to a high voltage switch in the high-frequency pulsed power supply 826 to output a high voltage pulse. This high-voltage pulse output is delivered to a relay 840, which is set to receive the same, and the signal is in turn transmitted to the sensing section 18. In a preferred form, the signal sent to the sensing section 18 from the high-frequency pulser section 820 is a 385-volt square-wave pulse that causes the high-frequency transducer 40 to initiate the high-frequency ultrasonic pulse for interrogation of the sample container. This high-voltage pulse output signal is transmitted the sensing section 18. Return echo(es) are received back from the sensing section 18 and sent through the receiver board 900 to the digital board 1000 for digitization, following which they are communicated through the PicoWeb™ interface board 1100 to the host computer 14.

Substantially the same sequence occurs when a low-frequency activating signal 832 is received as the initial sync or trigger signal (which would occur when the low-frequency transducer section is mounted in the gun assembly). In this configuration, the low-frequency initiating signal 832 is directed as a low-frequency input to its related amplifier 834, the output of which then goes to the low-frequency pulse power supply 836, which produces a burst pulse. In the preferred embodiment, this burst pulse comprises a sinusoidal waveform or tone burst of from several to multiple cycles, each having a voltage of about 600 volts.

The relay 840 receives the output signal of the low-frequency pulse power supply and in turn transmits this signal to the sensing section 18. This pulse signal then activates the low-frequency transducer 40, which, at the time of activation, is mounted in the gun assembly 12. As in the case of the high-frequency pulse, the low-frequency signal is transmitted to the receiver board 900, is digitized by the digital board 1000, and is communicated to the computer 14 through the PicoWeb™ interface board 1100.

It will be readily understood by those skilled in the art that within the broader scope of this invention, the operating parameters discussed herein in reference to the present embodiment of the present invention may be varied depending on the application.

For example, the voltage of the high-frequency pulse 822 could have a voltage level as high as 400, 450, 500, 600, 700, 800, 900 or possibly 1,000 volts, or possibly as low as 350, 300, 250, 200 or 150 volts or lower. In like manner, various parameters of the low-frequency burst could be varied. For example, the voltage of this low-frequency burst 832 could be as low as 200, 300, 400, 500 volts on the low side or as high as 700, 800, 900, 1,000 volts or higher on the high side.

ii. The Receiver Circuit Board 900.

Reference is now made to FIG. 9 showing a block diagram of the receiver board 900. After the pulse from the pulser board 800 is delivered to the transducer 40 to generate the low- or high-frequency ultrasonic pulse that interrogates a container undergoing inspection, one or more return acoustic echoes are received by the transducer 40 and are translated into an analog signal(s). The analog signal(s) is received by the receiver board 900 and delivered to the digital board 1000 (FIG. 10) as an analog signal. Digitization of the analog signal occurs by means of an analog-to-digital converter 1020 found on the digital board 1000.

In FIG. 9, the input signal to the receiver circuit board 900 is received from the sensor section 18 and is directed to a voltage limiter 920 which protects the receiver board 900 from the high amplitude transmit pulse(s), but still allows the low amplitude echoes (<1 volt) to pass. As indicated above, a return signal may comprise one or more signal components as a result of the acoustic echo or echoes being returned.

The return signal 910 received through the voltage limiter 920 is directed to a pre-amp 930 and the amplified signal output from the pre-amp 930 is directed to and through a high-pass filter 940 which passes frequencies of 100 KHz and above. The signal output from the high-pass filter 940 is then directed to a variable-gain amplifier 950, then through a post-gain amplifier 960 to the digital board 1000.

The variable-gain amplifier 950 in this receiver circuit 900 is under the control of the digital board 1000, and the user/operator of the inspection apparatus can enter commands that cause the received signal 910 to be amplified via adjustments to the variable-gain amplifier 950.

The post-gain amplifier 960 is or may be conventional. In this specific embodiment, there is a two-stage, post-gain amplifier 960, with a first stage providing a 20 dB increase in signal strength and a second stage providing another 20 dB increase in signal strength.

The output from the receiver board 900 is an amplified analog signal that is then directed to the digital board 1000 to be converted into a digital signal by means of an analog-to-digital converter 1020 (FIG. 10).

iii. Digital Board 1000.

Reference is now made to FIG. 10 showing a block diagram of the digital board 1000. A description will be made of the overall functions of each of the components shown in the block diagram of FIG. 10. Then there will be a review of the overall operation of the digital board 1000.

On the digital board 1000, a power regulator (DC-to-DC converter) 1005 receives a +12-volt power input from a power source (e.g., a battery or other power source) 22. From this single input power source voltage, the power regulator 1005 provides a plurality of output voltages based on requirements of the various components in the circuit section 20 and in the inspection apparatus 10. More specifically, the regulator/converter circuit 1005, converts the +12-volt power input source voltage into five specific voltage outputs, a first voltage being a $^+$10-volt output, a second and third voltage being $^+$5-volt outputs, and a fourth and fifth voltage being $^+$3.3-volt outputs.

In the first case, the regulator 1005 converts a +12-volt input source voltage received from the power source 22 to a $^+$10-volt output that drives major circuits on the pulser board 800, the receiver board 900, and digital board. More specifically, the $^+$10-volt output voltage from the regulator 1005 enables and powers the HF pulser circuit 820 and LF pulser circuit 830 located on the pulser board 800, as well as components on the receiver board 900. On the receiver board 900, the $^+$10-volt output is delivered through the digital board interface 1015 to the individual components, which include the preamp 930, the high-pass filter 940, the variable-gain amplifier 950, and the post-gain amplifier 960, respectively. In the preferred configuration, the $^+$10 volt output from the regulator 1005 also powers the D/A converter 1050 and the digital interface circuit (pulser/receiver board interface) 1015, the latter component providing the critical interface for transfer of data and information between the pulser board 800, the receiver board 900, and the digital board 1000.

The converter 1005 further provides two $^+$5-volt output voltages. The first $^+$5-volt output (e.g., $^+$5V_HV) is provided as an input to the high-frequency pulser section 820 on the pulser board 800 that results in a 385-volt square wave high-voltage output.

More specifically, the voltage is delivered through the digital board interface 1015 to the pulser board 800, where it is input to the high-frequency pulsed power supply circuit 826. The second $^+$5-volt output (e.g., $^+$5V_PICO) from the converter 1005 is delivered to the PicoWeb™ interface logic circuit 1010 on the digital board 1000. The converter 1005 further provides two $^+$3.3-volt outputs. The first $^+$3.3-volt output (e.g., $^+$VA) is delivered to, and powers, various analog circuits, including the A/D converter 1020 on the digital board 1000. The second $^+$3.3-volt output (e.g., $^+$VD) is delivered to, and powers, other digital board 1000 circuits, including the FPGA component 1025, the microprocessor 1030, the FIFO component 1040, the Temperature Sensor A/D 1045, the EEPROM circuit section 1055, and the RAM component 1060.

The digital board 1000 further comprises a microprocessor component 1030 (microcontroller) that serves a primary function of receiving, processing, and directing signals and/or information transmitted to and from the circuit section 20. The microprocessor 1030 also provides for control of data acquisition and user interface functions.

The microprocessor 1030 further receives and processes various power and signal inputs. For example, there is an operative connection between the microcontroller 1030 and the converter 1005. The converter 1005 is turned on or off by an enabling signal (e.g, ANALOG_ON) sent from the microcontroller 1030 to the converter 1005.

The microprocessor 1030 of the digital board 1000 may be of a conventional type. In the preferred embodiment, the microprocessor 1030 is currently an MSP-430F OTP/EPROM chip, commercially available from Texas Instruments (Dallas, Tex. 75243-4136, USA).

It will be understood by those skilled in the art that other comparable components may provide the functions required of the microprocessor. Thus, no limitation in element type, function, or scope is explicitly or inherently implied or suggested herein by the use of a particular component.

As shown in FIG. 10, the microprocessor 1030 is operatively connected to, and interacts with, a multitude of components on the digital board 1000, including the Power Regulator 1005, the FPGA 1025, the FIFO memory circuit 1040, the EEPROM circuit 1055, the LED Display Connector 1075, and the trigger switch connector 1070. The microprocessor 1030 also communicates and interacts with the various components of the Pulser board 800 and the Receiver board 900 by means of the Digital Board Interface 1015.

The microprocessor 1030 further interacts with the PicoWeb™ board by means of the PicoWeb interface 1010 found on the digital board 1000, operatively connecting with the PicoWeb™ board through the PicoWeb interface connector 1085 and the PicoWeb parallel I/O connector 1110.

The microprocessor 1030 includes a bus element comprising eight data lines and fourteen address lines, whereby it can interact, transmitting data and information between the various components under its operative control.

For example, a primary function of the microprocessor 1030 is to transmit converted/digitized signal data from the A/D converter 1020. Further, as shown in FIG. 10., the microprocessor 1030 also receives and transmits signal data to and from the EEPROM Memory circuit 1055, the FIFO memory circuit 1040. The microcontroller 1030 also transmits an enabling signal (e.g., HV ON) through the Pulser board connector 1015 to the high-voltage circuit 820 of the Pulser Board 800 to turn the high voltage on.

The microprocessor 1030 on the digital board 1000 is also able to recognize and/or determine the type of sensor transducer (whether LF or HF) 40 attached to the apparatus 10.

The microprocessor 1030 detects and receives a signal (e.g., TYPE RLY) via the Pulser/Receiver board connector 1015 indicating the type of sensor transducer (whether LF or HF) 40 attached to the apparatus 10, as well as the digitized temperature waveform signals from the temperature A/D converter 1045. The microprocessor 1030 processes the input signals received from the Receiver Board 800 as to sensor type, as well as the output signals from the temperature A/D circuit 1045 on the digital board 1000.

The microprocessor 1030 (FIG. 10) is also responsible for sending an enabling signal (e.g., FIRE) to the FPGA 1025 that initializes and synchronizes the circuit, resulting in the HF and LF pulse-trigger/sync signals being output and transmitted to the HF signal channel 820 or the LF signal channel 830 of the pulser board 800, respectively. The signal further tells the FPGA 1025 when to begin its repetition cycle.

The microprocessor 1030 is also configured to communicate with a Debug connector 1080 via a serial communication circuit 1065. This circuit (e.g., microprocessor 1030 to debug connector 1080) is used only during programming to facilitate troubleshooting of the microprocessor 1030 and/or apparatus 10.

The microprocessor 1030 also interacts with the LED display element section 1075 on the digital board 1000, directing signals (e.g., FIRE, ERROR, etc.) to the LED display element section 1075. In the preferred embodiment, the LED display element section 1075 comprises three individual LEDs, a first LED illuminating when the inspection apparatus 10 is first powered, a second LED illuminating when a signal (e.g., FIRE) is received indicating the inspection apparatus 10 has been activated or when waveform data are being acquired, and a third LED illuminating when an error signal (e.g., ERROR) is encountered.

The microprocessor 1030 further receives, processes, and transmits interrogation (e.g., waveform) signal data for the inspection apparatus 10, when "the trigger switch 77 (operatively connected to the trigger switch connector 1070 on the digital board 1000) is activated by the operator."

Other important functions of the microprocessor 1030 include interaction/communication with the FIFO data buffer circuit 1040, the EEPROM memory circuit 1055, as well as the PicoWeb™ Interface logic circuit 1010.

The Field Programmable Gate Array (or FPGA) 1025, another component of the digital board 1000, is operatively connected to the microprocessor 1030. The FPGA 1025 functions to control: 1) delay time, 2) digitizing rate, 3) frequency of the burst cycle emitted by the lower frequency transducer section 58, and 4) width of the high-frequency pulse of the high-frequency transducer section 40. The FPGA 1025 is further hard-coded to perform its functions, and communicates/interacts with the microcontroller 1030 through two virtual serial ports (communication interlinks). In the preferred embodiment, serial communication is performed using a "2-wire" or "I$^2$C" protocol. In this preferred configuration, the first serial interlink (e.g., SDA) transmits operator control and/or configuration data from the microcontroller 1030 to the FPGA 1025. The second serial interlink (FPGA_SCL) shifts the configuration data into the FPGA 1025 making those parameters available for use by the apparatus 10. In this manner, operation parameters (e.g., pulse width, timing and frequency of delivery of pulses, how often pulses are delivered, the number of pulses in a burst, etc.) of the respective HF pulser circuit 820 and LF pulser circuit 830 are delivered to, and communicated through, the FPGA 1025 to the inspection apparatus 10.

The FPGA 1025 is unique in that it can be reprogrammed, or the programming can be modified to perform additional functions. Modifications to the FPGA (or "gate array") 1025 programming are made through a JTAG interface element (not shown), comprising four additional communication lines (e.g., TDO_FPGA, TMS_FPGA, TDI_FPGA, and TCK_FPGA). During normal operation of the apparatus 10, the JTAG interface is not used.

The FPGA component 1025 is responsible for initiating the LF and HF trigger/sync pulses (e.g., PULSER_TRIG_LF and PULSER_TRIG_HF, respectively) as inputs to the respective HF circuit 820 and LF circuit 830 sections of the pulser board 800. The FPGA 1040 is operatively connected to the pulser board interface connector 1015 (See FIG. 10), enabling the trigger pulses to reach the required subsections of the pulser control circuit 800.

The FPGA 1025 further comprises an oscillator/amplifier (not shown) that delivers a 20 MHz root frequency to the FPGA 1025, a frequency from which all other frequencies employed within the apparatus 10 are derived.

A clock signal (CLK) from the FPGA 1025 controls the actual timing functions related to delay, intervals, frequencies, and pulse widths of the trigger pulse signals delivered to the LF circuit 820 and HF circuit 830 sections of the pulser board 800, respectively. The FPGA 1025 clock signal also controls repetition rate and the number of pulses in a burst, etc.

The clock signal (CLK) from the FPGA 1025 further controls and synchronizes the timing functions for other important circuits. During normal operation, for example, the clock signal (CLK) from the FPGA 1025 is transmitted to the FIFO data transmission section 1040 thereby controlling frequency and timing functions for this circuit. The timing clock signal (CLK) from the FPGA 1025 is also directed to the analog-to-digital converter section 1020. Every time the clock signal (CLK) is a "falling" signal (going from a high level to a low level), the received analog input (waveform) signal is read, directed into the analog-to-digital converter 1020, and digitized into an 8-bit result value. The digitized value is then transmitted and written to the FIFO data buffer 1040 through one of two data bus elements in the FIFO circuit 1040.

In the preferred embodiment, the FIFO 1040 comprises two "or" gates, the first gate being enabled to receive and read a clock signal (e.g., PICO FIFO RCLK) from the PicoWeb™ board 1100 during normal operation of the apparatus 10, or to secondly read and receive a clock signal (e.g., FIFO RCLK) from the microprocessor 1030 when testing the communication pathway between the microprocessor 1030 and the FIFO 1040. A second "or" gate receives the normal clock signal (CLK) from the FPGA section 1040 controlling the timing of the pulser sections during operation of the apparatus 10. The FPGA 1040 transmits the timing clock signal (CLK) to the FIFO 1040 through the second of two "or" gates located within the FIFO circuit 1040, the first "or" gate being reserved for troubleshooting interactions with the microcontroller 1030, as well as normal communications with the PicoWeb™ board 1100 during operation.

The FIFO data transmission section 1040 operates on a "first-in/first-out" basis to allow data to be input at a fast rate and to be extracted at a slower rate, i.e., upon request. The waveform signal inputs to the FIFO 1040 come from the analog-to-digital converter 1020 (A/D converter 1020) as shown in FIG. 10. The FIFO data section 1040 does not make use of specific address lines as are utilized in the RAM component 1060. In the FIFO 1040, a data pointer is incremented upon arrival of each new data bit. Under the preferred operating conditions, when the FIFO component 1040 is full or a new clock cycle initiates, the waveform data are retrieved, read, and transmitted via parallel data bus lines to the PicoWeb™ board 1100. As a new cycle initiates, the data locator/pointer is also reset and new waveform data can enter the FIFO circuit 1040.

In the preferred embodiment, the two bus elements of the FIFO circuit 1040 each comprise eight data lines. Each line transfers 1-bit of data, transferring up to 1-byte of data each per clock cycle. Each of the digital data bus sections of the FIFO circuit 1040 is operatively connected with the microcontroller 1030, as well as the PicoWeb™ interface logic circuit 1010. When the timing clock signal (CLK) received by the FIFO 1040 goes from low to high, waveform data stored in the FIFO 1040 are read and output from the FIFO 1040 through the digital bus elements, transmitted through the PicoWeb™ interface logic circuit 1010, and received through the parallel I/O connector 1110 to the PicoWeb™ board 1100.

In this manner, waveform data are transmitted to the PicoWeb™ board 1100. A waveform is ultimately delivered to the host PC 14 for further processing and/or analysis through the microcontroller 1120 and Ethernet controller 1130 on the PicoWeb™ board 1100.

The temperature sensor analog-to-digital (A/D) converter 1045 is located on the digital board 1000. As indicated earlier, the thermistor 49 is mounted in the transducer assembly (unit) 58. The thermistor 49 transmits an analog signal (e.g., THERMISTER_H) representing the temperature reading to the temperature sensor analog-to-digital converter 1045 on the digital board 1000, which converts this analog signal to a digital signal. The temperature sensor A/D 1045 is under the control of the microcontroller 1030, which will automatically and periodically interrogate the temperature sensor A/D 1045 and, with each waveform request received from the host computer 14, transmit the digitized temperature reading to the host computer 14.

An operator has the latitude to manually request a temperature reading by sending a user command waveform request for an update of the control configuration.

The waveform amplitude D/A converter 1050 (FIG. 10) serves a principal function of assisting in the transmission of analog signals of proper and adequate intensity to the receiver board 900 via the pulser/receiver board interface connector 1015. The waveform amplitude D/A converter 1050 (FIG. 10) has an operative connection to the microprocessor 1030, and interacts with the receiver board 900, communicating by way of the 10-pin pulser/receiver connector 1015 on the digital board (FIG. 10). The D/A converter 1050 also interacts with the pulser board 900 via this same connector 1015, and is powered by the $^+$10-volt source from the regulator 1005.

In the preferred embodiment, when a weak signal received from the transducer section 58 is provided to the digital board 1000 from the receiver board 900, as for example, when a received acoustic wave is highly attenuated due to its passing through a long distance, the operator has the option of entering a request into the computer (e.g., PDA, laptop, desktop, etc.) 14 instructing the microcontroller 1030 to provide and/or retrieve a higher signal amplitude that can be more easily read and processed.

To attain this increase in waveform amplitude, an operator request is input in the computer 14. A command from the microcontroller 1030 is sent to the D/A converter 1050, which subsequently transmits a request signal (GAIN_SET) through the pulser/receiver board interface connector 1015 to the variable gain amplifier 950 on the receiver board 900. In response, a higher amplitude analog signal is transmitted back to the A/D converter 1020 on the digital board 1000. Since the microcontroller 1030 only provides (or outputs) digital signals, the D/A converter 1050 is responsible for transmitting the appropriate analog signal to the receiver board 900.

A non-volatile memory EEPROM storage element 1055 stores operating settings, and other setup information for the inspection apparatus 10, retaining such information when the apparatus 10 is shut-down or if power is lost. The EEPROM component 1055 allows the operator to adjust and/or establish settings in the apparatus 10 that can be stored in the gun 12 during operation. When power to the gun 12 is lost or shut off, operating parameters and configuration information are retained by the EEPROM 1055 so that when the operator again powers the gun assembly 12, the same pre-selected settings and configuration information are retained and made available to the operator. Operating parameters are retained unless or until the operator chooses to change or modify them.

The RAM component 1060 on the digital circuit section 1000 serves as a temporary memory buffer and data exchange location during troubleshooting or testing of the apparatus 10. The RAM component 1060 has operative connections with the microcontroller 1035 and the FIFO memory circuit 1040, located on the digital circuit section 1000, as well as the host computer 14. The RAM component 1060 comprises 15 address lines to uniquely identify, direct, and/or store a variety of acquired data streams, including operation information, diagnostic information, and/or other data analysis information. The RAM component further comprises 8 data lines in order to interact with, and transmit data to, the microcontroller 1035, the FIFO memory circuit 1040, and/or the host computer 14. User commands and/or requests input by an operator interact with the RAM component 1060 by way of the computer 14 to the microcontroller 1030. Further, any overflow waveform data stored in the RAM are transmitted to the FIFO section 1040 via the data bus located on the RAM component 1060. Data received by the FIFO circuit 1040 from the RAM circuit 1060 may then be transmitted to the host computer 14 following a request received from the microcontroller 1030. In this manner, information is made available through the computer display to the operator.

In the preferred configuration, (similar to that used for the FPGA component 1025), the temperature sensor A/D 1045, the waveform amplitude D/A converter 1050, and the EEPROM 1055 all interact/communicate with the microcontroller 1030 using an "I$^2$C" protocol, whereby a $1^{st}$ serial data (SDA) line is used to transfer data, and a $2^{nd}$ serial clock (SCL) line is used to control the timing of the data transfer. Each component has a unique TCP/IP protocol address address. When an instruction is received from the microcontroller 1030, the instruction is directed to the correct circuit section thus effecting the appropriate control. With each clock cycle and/or request, data in these components are transferred via the SDA serially to the microcontroller 1030. Data are subsequently transmitted through the PicoWeb interface logic circuit 1010 and PicoWeb connector 1085 located on the digital board 1000 to the PicoWeb™ board 1100. From the PicoWeb™ board 1100, data are packaged and transmitted via Ethernet to the computer 14. Details of the Ethernet communication pathway with the host computer 14 are described in more detail below.

The trigger switch circuit portion 1070 (trigger switch connector 1070) responds to the switch assembly 23 mounted in the gun pistol grip 26 of the gun assembly 12. The switch assembly 23 is activated by a signal (e.g., ACTIVATE_SW) when an operator squeezes the trigger 72 that also activates the trigger switch 77. Once the switch assembly 23 is activated, a signal (e.g., TEST) is sent to the microcontroller 1030 that initiates and tests the operation of the apparatus 10, putting it into a ready mode.

With regard to the overall operation of the apparatus 10, when the apparatus 10 is not in use, unless powered down, the microcontroller 1030 goes into a low-power-operating mode to conserve energy. During low-demand or non-operating periods, the microcontroller 1030 also signals and controls other components in the apparatus 10, resulting in a similar low-power or power-down mode.

In a condition of low-demand, for example, the microcontroller 1030 can transmit a signal (e.g., AD_SLEEP) to the A/D converter 1020, placing it in a temporary standby or sleep mode.

The microcontroller 1030 also controls other shut-down points, including each of the voltage output circuits of the regulator/converter 1005. For example, a signal (5V_ON) may be sent to the first 5-volt output circuit of the regulator/converter 1005, turning the digital board interface 1015 on or off, thereby conserving power. Additionally, a signal (PICO_ON) may be sent to the $2^{nd}$ 5-volt output circuit in the regulator/converter 1005, turning the PicoWeb™ board 1100 on or off.

As shown in FIG. 10, the microprocessor 1030 on the digital board 1000 is further operatively connected to a LED display section (FIG. 10) 1075. The LED display section 1075 comprises several LED elements (not shown) that display and/or provide information to the operator.

In the preferred embodiment, the LED display section 1075 includes a first power LED, a second activation LED, and a third error signal LED. The power LED, when illuminated, indicates to an operator that power is available to the apparatus 10. The activation LED illuminates when the trigger assembly 72 of the apparatus 10 is pressed, informing an operator that waveform data are being acquired, and that the apparatus 10 is functioning properly. An error signal LED, a third LED in the circuit, illuminates when an error occurs during the data acquisition process.

The various LED displays can be color coded, if desired, to indicate the various functions. Also included in the LED section 1075 is a multi-vibrator (not shown) that takes very high-frequency pulses and translates them into longer pulses with longer gaps between the pulses. In this configuration, the duration of the LED light pulses and the spacing between these light pulses permits a user to optionally observe the LED signal displays in a "blinking" light mode.

The digital board 1000, PicoWeb™ board 1100, and the host computer 14 communicate and interact with each other by means of both a parallel communication pathway and a serial communication pathway.

The parallel pathway comprises a path from the digital board 1000 to the PicoWeb™ board 1100 through the PicoWeb™ interface to a parallel I/O connector 1110 on the PicoWeb™ Board 1100. The serial pathway comprises a serial circuit 1140, and further includes an Ethernet controller 1130 and an Ethernet connector 1150, both of which are located on the PicoWeb™ board 1100. Both communication pathways are further described below.

d) The Interface Board (PicoWeb™ Interface Board) 1100.

Figure 11:
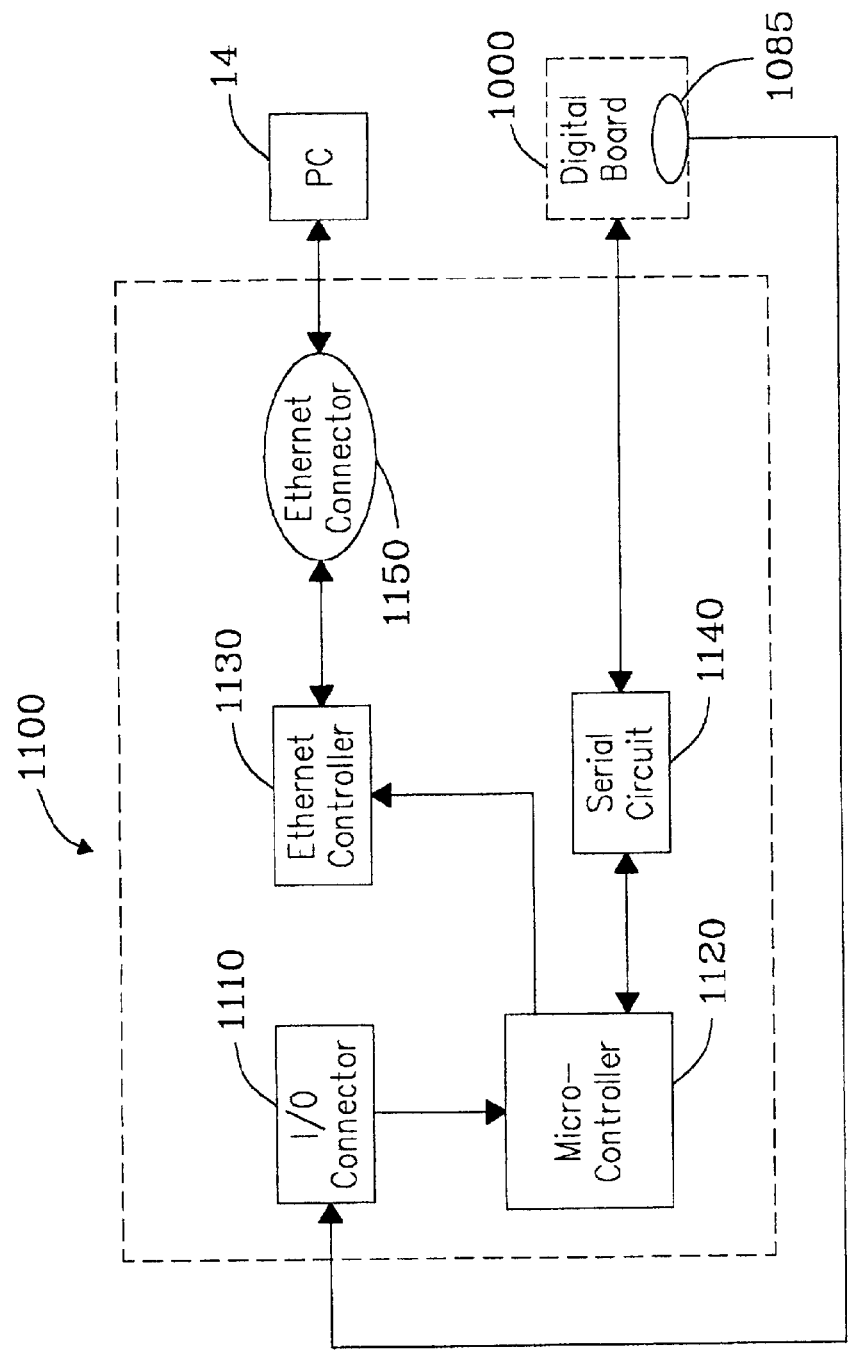
FIG. 11 is a block diagram of the PicoWeb™ board of the circuit board section.

Reference is now made to FIG. 11 of the drawings. The circuit board of FIG. 11 is, or may be, the same as, or similar to, a commercially available circuit board. For example, the preferred embodiment is a PicoWeb™ interface board from Lightner Engineering (San Diego, Calif.).

The main function of the PicoWeb™ Interface board 1100 is to receive information from the digital board 1000 and place it in a format that can be communicated properly to the host computer 14. The PicoWeb™ Interface board 1100 also passes information, commands, and requests from the computer 14 back to the digital board 1000.

The PicoWeb™ board 1100 is operatively connected to the digital board 1000 by means of a 25-pin input/output (e.g., I/O) parallel connector 1110 located on the PicoWeb™ board 1100. Digitized signal or waveform data are transmitted through the PicoWeb™ interface 1010 on the digital board 1000 through the I/O connector 1110 on the PicoWeb™ board 1100 to an 8-bit microcontroller circuit 1120, which packages and prepares the data with the proper Ethernet (TCP/IP or UDP) protocols (including protocol requirements, header information, and packet format, etc.) for transfer to the Ethernet controller 1130. From the controller 1130, data are then transmitted through the Ethernet connector 1150 to the host computer 14, where the waveform is reassembled and/or data are further processed.

The microcontroller 1120 on the PicoWeb™ board 1100 serves as a communication and programming center for the PicoWeb™ board 1100, processing and transmitting data with the necessary and proper communication protocols to and from the host computer 14.

In the preferred embodiment, the microcontroller 1120 comprises an 8-bit MIPS RISC processor, optimally configured to include, at a minimum, 8 Kb flash program memory, 512 bytes EEPROM memory, and 512 bytes RAM memory. The microcontroller is, or may be, the same as, or similar to, a commercially available circuit board. For example, in the present embodiment, an 8-bit AVR microcontroller 1120 is currently integrated with a PicoWeb™ interface board 1100, available from Lightner Engineering (San Diego, Calif.).

In the preferred embodiment, the microcontroller 1120 further comprises: 1) a parallel data driver sequence in order to transfer data to and from the digital board 1000 through the PicoWeb interface 1010 and parallel I/O connector 1110, and 2) a serial (e.g., RS-232) driver sequence in order to transmit information through the serial interface circuit 1140 to the digital board microcontroller 1030.

As indicated, in addition to receipt of data through the I/O connector 1110, the PicoWeb™ board 1100 microcontroller 1120 also processes configuration, setup, and/or command information received through the serial circuit 1140, introducing it in the correct format to the Ethernet controller 1130 for communication by way of the Ethernet connector 1150 to and from the host computer 14.

As disclosed, the PicoWeb™ board 1100 microcontroller 1120 is operatively connected to a serial interface circuit 1140. In the preferred configuration, the serial interface is an RS-232 circuit 1140, located on, and integrated with, the PicoWeb™ board 1100. The serial interface 1140 serves as the primary communication pathway between the PicoWeb™ board and digital board 1000 for transmitting control, configuration, and/or setup information from the host computer 14 to the microcontroller 1030 on the digital board 1000. In the preferred embodiment, under normal operation, user commands and other control or configuration information are first sent (under a TCP/IP protocol) from the host computer through the Ethernet connector 1150 (e.g., 10-Base-T connector 1150) to the Ethernet Controller 1130, where they are transmitted to and received by a microcontroller 1120 (e.g., 8-bit AVR microcontroller 1120). The configuration information is subsequently transmitted through the serial interface (e.g., RS-232) 1140 on the PicoWeb™ board 1100 to the microcontroller 1030 on the digital board 1000, and written or stored to the EEPROM memory circuit 1055. Once received, the microcontroller 1030 echoes the current control configuration, along with an updated temperature reading received via serial data line (SDA) from the temperature A/D 1045 (or other updates from the EEPROM 1055 and amplitude D/A 1050 components), back to the host computer 14. The PicoWeb™ board 1100 microcontroller 1120 thus processes any configuration information received through the serial circuit 1140, introducing it in the correct format to the Ethernet controller 1130 for communication to and from the host computer 14 through the Ethernet connector 1150.

In the present embodiment, the serial interface 1140 circuit is the preferred pathway for transmission of user control and/or configuration information from the host computer 14. The serial interface (e.g., RS-232) circuit 1140 on the PicoWeb™ board 1100 transmits configuration and/or control information received by the microcontroller 1120 of the PicoWeb™ board 1100 from the host computer 14 and transmits it to the microprocessor 1030 on the digital board 1000. The microcontroller 1030 echoes and/or returns any updated information back to the microcontroller 1120 of the PicoWeb™ board 1100, which subsequently transmits the updated information back to the host computer 14. The RS-232 interlink (interface) 1140 on the PicoWeb™ board 1100 thus enables the microcontroller 1120 of the PicoWeb™ board 1100 to communicate with the microcontroller 1030 on the digital board 1000.

The microcontroller 1120 (FIG. 11) on the PicoWeb™ board 1100 also interacts with the digital board 1000 by means of the PicoWeb™ board interface 1010 on the digital board 1000 and the parallel I/O connector 1110 on the PicoWeb™ board 1100.

The parallel I/O connector 1110 to PicoWeb™ interface 1010 circuit is the primary route for transmitting waveform and/or signal data, as distinguished from control configuration data/information. In the preferred embodiment, the PicoWeb™ board 1100 receives digitized waveform (signal) data previously stored and/or buffered in the FIFO circuit 1040 on the digital board 1000. Data in the FIFO 1040 are first transmitted through the PicoWeb™ board interface 1010 circuit and the PicoWeb connector 1085 on the digital board 1000. Data are then ported through the parallel I/O connector 1110 on the PicoWeb™ board 1100 and received by the AVR microcontroller 1120 for proper data packaging. The packaged data are then transmitted from the microcontroller 1120 to the Ethernet controller 1130, further through the Ethernet connector 1150, where the data are received by the host computer (PDA, laptop, desktop, or other host) 14 for further processing.

e) The Host Computer 14.

As indicated in the text, the inspection apparatus 10 can be integrated for use with any properly configured host computer 14 (e.g., PDA, laptop, desktop, etc). In one embodiment of the present invention suited to automated processes such as system monitoring and/or control applications, the host computer 14 may be a laptop or a desktop configuration. In a preferred embodiment, the computer 14 is currently a PDA (Personal Digital Assistant) that can be mounted on the upper rear portion 84 of the gun assembly 12, or possibly carried by the intended user/operator on a belt, or other carrying device. In the preferred configuration, the host computer 14 (PDA) is located so that the graphic interface of the computer can be readily observed or be readily accessible by the operator of the apparatus 10.

It is believed that a clearer understanding of the functions performed by the computer will be obtained by first describing the general functions of the computer, the waveforms that it generates, the method of actually making an inspection, and showing how the operation of the gun assembly 12 relates to the functions of the host computer 14. After that, there will be a more detailed description of how some of the functions of the computer 14 are actually accomplished.

As indicated previously in this text, the computer 14 serves a number of functions, with a primary function being to identify the velocity of the ultrasonic pulse that travels through a material in a container relative to the temperature of the same material in the container. The ambient temperature is measured so that an adjustment can be made in the actual velocity determination prior to the database search and match-up, since the propagation of sound in various materials differs as a function of temperature. In some instances, for example, the velocity will increase as the temperature increases, and in other instances the velocity would decrease when the temperature is raised.

Velocity is determined in the host computer 14 by ascertaining the time-of-flight of the ultrasonic pulse (i.e. the time taken going from one location to another) and correlating this time with the distance traveled by the pulse. When both the time-of-flight and the distance are known, then the velocity can be calculated, which resultant velocity is then entered into the host computer 14. As indicated previously, the velocity determination is accomplished by placing the gun assembly 12 so that the front contact surface 38 of the transducer 40 is pressed against the near wall of the container, and by sending an acoustic pulse from the transducer so that the ultrasonic pulse travels through the container to the far wall so that an acoustic echo travels back to the transducer 40. Often, a second echo will be generated when the echo traveling back to the near wall is reflected back again to the far wall which in turn results in the second acoustic echo traveling back to the transducer 40.

Figure 12:
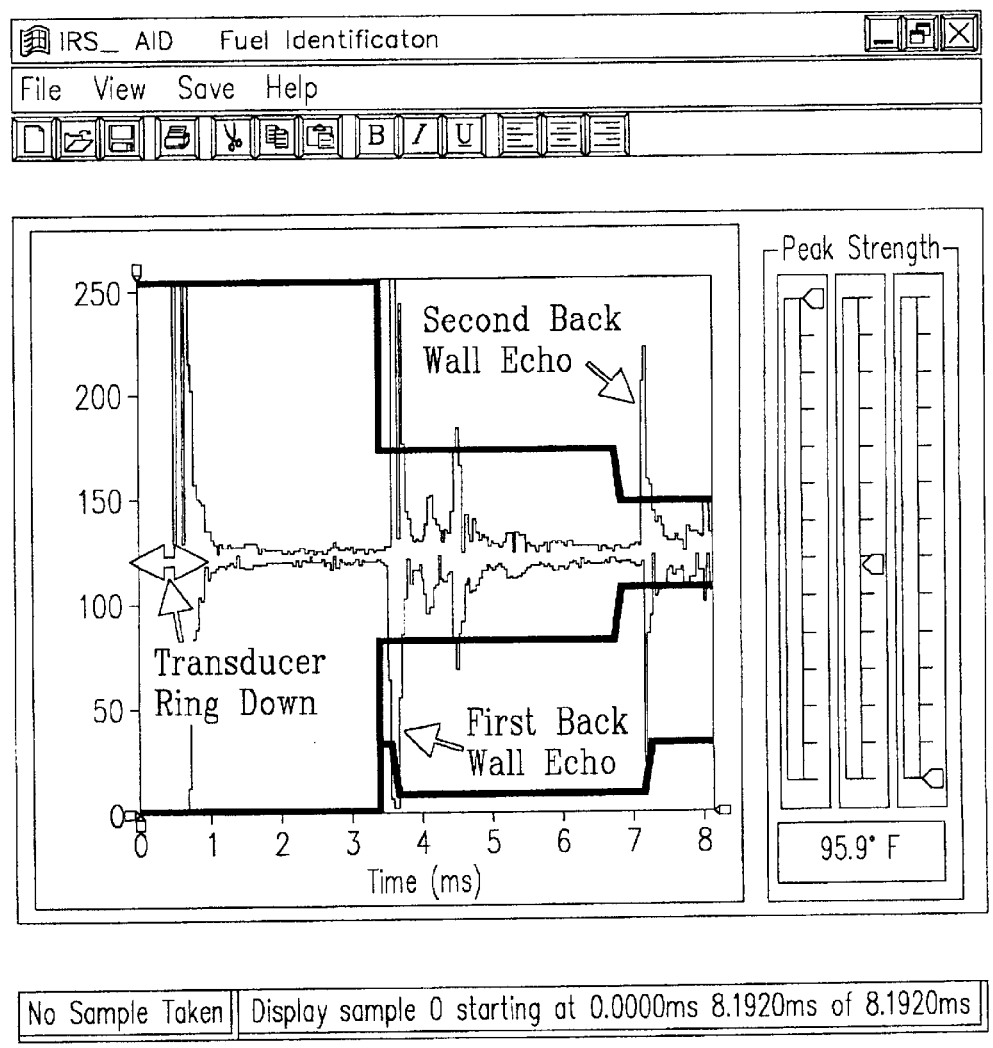
FIGS. 12 and 13 are two views of the graphic interface of the computer, showing typical waveforms that are developed in the computer.

Reference is now made to FIG. 12, which shows a typical waveform displayed on the graphic display (i.e., interface) of the computer 14. This waveform presented on the display is derived from the analog signal received from the transducer 40, which is translated into a digital signal by the digital board 1000, which in turn is received by, and is then presented as a waveform on the display screen of the host computer 14.

At the very left side of FIG. 12, at the zero point (location) in time, the start of a first peak representing a large acoustic reflection pulse can be seen (i.e., on the display). The reflection pulse (or wave) is first transmitted from the transducer 40 with which the transducer 40 is in contact to the near wall and immediately back to the transducer 40. The pulse coming back from the near wall of the container comprises a series of oscillations, which in FIG. 12 is indicated as the "transducer ring-down" portion of the waveform. Immediately to the right of the ring-down zone, the waveform comprises low amplitude oscillations, which are due mainly to background noise and/or continued oscillations caused by the receipt of the initial waveform.

When the ultrasonic (acoustic) pulse has completed its path of travel from the near wall to the far wall of the container and then back to the near wall, a peak is seen in the display corresponding to the acoustic waveform that, in FIG. 12, is designated as the "first back wall echo". It will be noted that there are continued oscillations after the presentation of this peak, which attenuate (diminish) in a left-to-right direction.

Then at the right hand side of the screen in FIG. 12 there is another later peak representing a second back wall echo, which is the result of the first acoustic echo being reflected from the front wall to the back wall and again reflected to the front wall.

Figure 13:
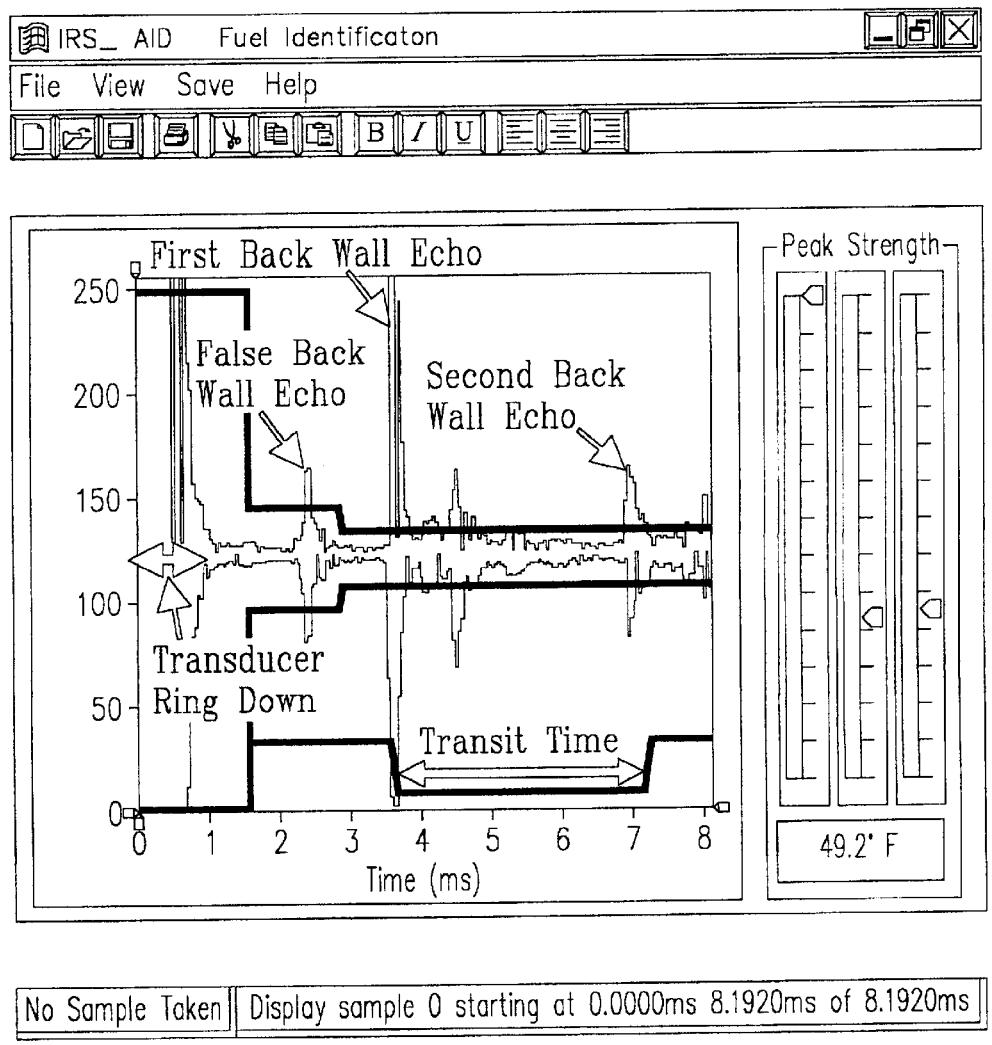

Attention is now directed to FIG. 13. It can be seen that the waveform of FIG. 13 is similar to that shown in FIG. 12 in that there is a ring-down area, a first back wall echo, and a second back wall echo, with a transit time being indicated between the first back wall echo and the second back wall echo. However in FIG. 13, also shown is what is designated as a "false back wall echo". This could occur, for example, by a pipe being within the container (e.g. possibly a pipe in a large tank of a tank car or an over-the-road tank truck). Alternatively, this could be from a concealed object (e.g., contraband) of some sort. When the ultrasonic pulse reaches a foreign object located in the container being inspected or tested, due to the fact that there is a differing material interface at the surface of the foreign object (acoustic impedance mismatch), there is an echo resulting from the ultrasonic pulse contacting that interface.

With the foregoing being given, the steps taken by an operator of the inspection apparatus 10 to conduct an inspection of a container or a number of containers can be presented.

As an example, an inspection may take place at a port of entry into the U.S., where incoming shipments are to be inspected by a customs officer. The first step is to identify the declared contents or materials present in a container to be inspected. This information can often be obtained from the manifest, or similar documentation relating to the shipment. For a large container, there may be various obstructions, such as internal baffles, weld lines, a double-wall tank, and possibly tanks with a fill level(s) lower than the center line point of inspection. If the location of any of these is known, then the operator can take this into account and position or place the gun so that the path of travel of the ultrasonic pulse toward the far wall and back is substantially unobstructed.

Figure 14:
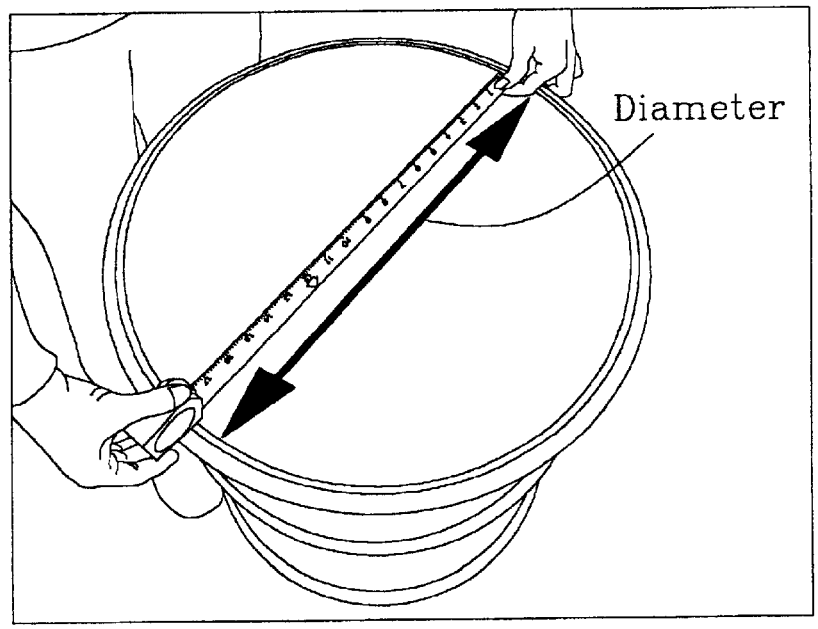
FIGS. 14, 15, and 16 illustrate the measurements taken of three different types of containers for determining the distance of the travel of the ultrasound pulse.
Figure 15:
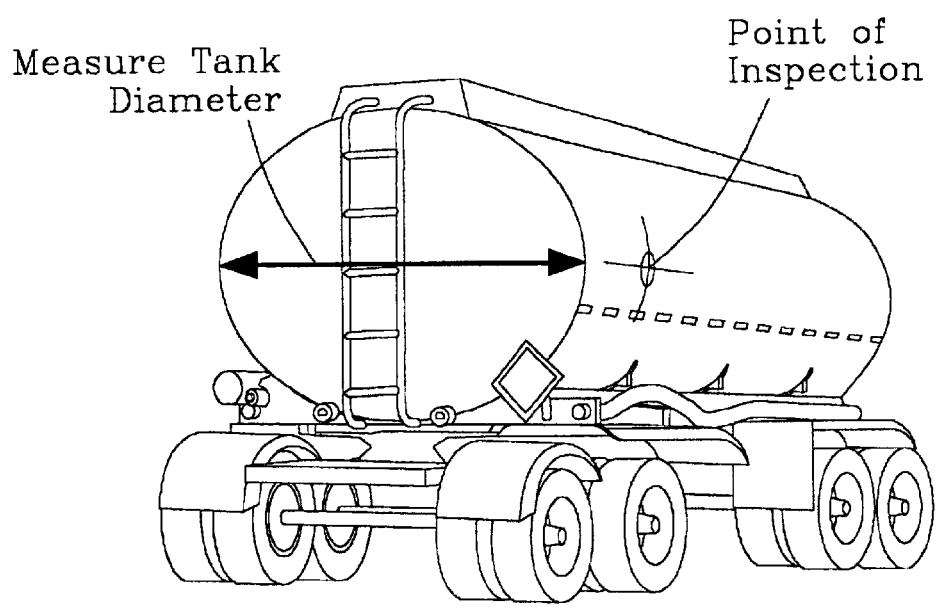
Figure 16:
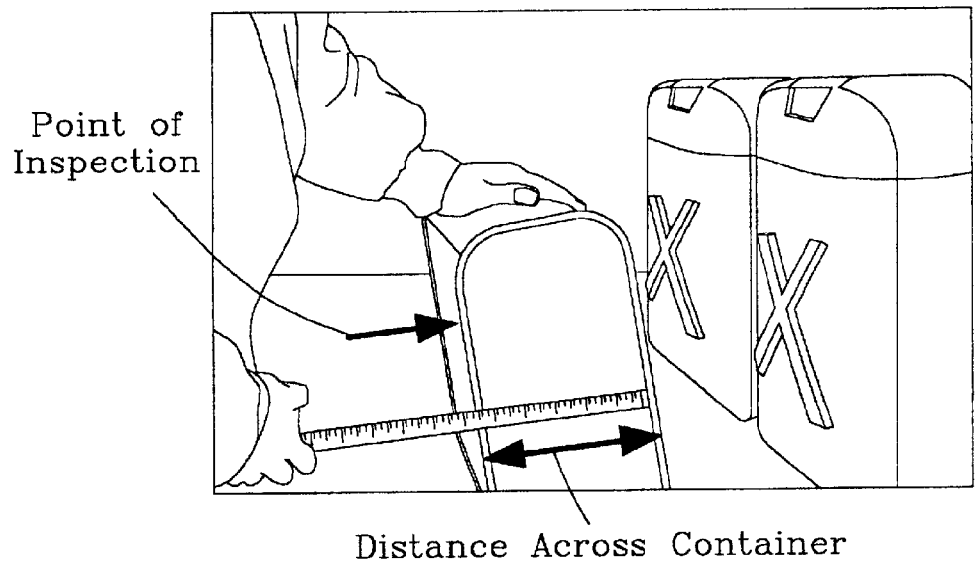

The next step is to ascertain or to determine the length of the path of travel of the acoustic pulse. For example, for a cylindrical or an oval container, the travel path length can be derived by ascertaining, and/or measuring the diameter. In FIG. 14 there is shown the taking of the measurement for a cylindrical drum; in FIG. 15, the measurement of the diameter of a large tank on a motorized vehicle is indicated, and also the point of inspection; and in FIG. 16, the point of inspection at a container having two parallel side surfaces is shown.

The next step is for the operator to make the proper inputs into the computer through the graphic interface (i.e. the screen). Reference is made to FIGS. 17*a* to 17*g*.

Figure 17A:
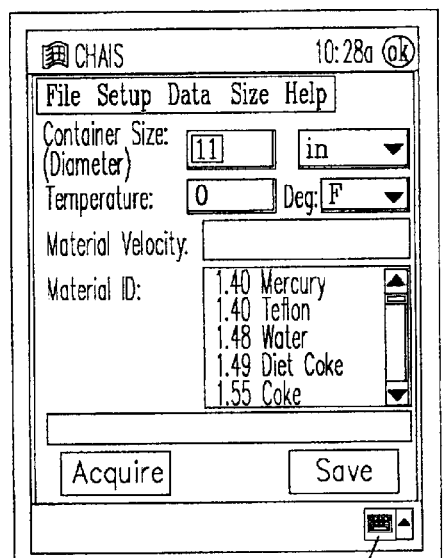
FIGS. 17a through 17g are views of the graphic interface of the computer showing the steps taken in preparing the gun assembly for an inspection operation.

In FIG. 17*a* access to the keypad is obtained by tapping the appropriate icon.

Figure 17B:
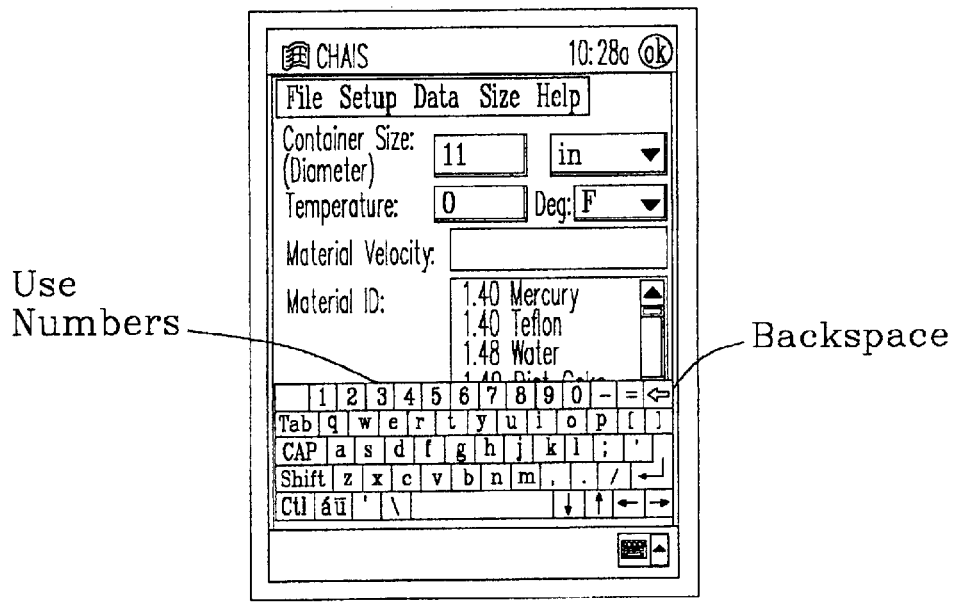

In FIG. 17*b* the diameter of the container can be introduced in the alpha numeric keypad.

Figure 17C:
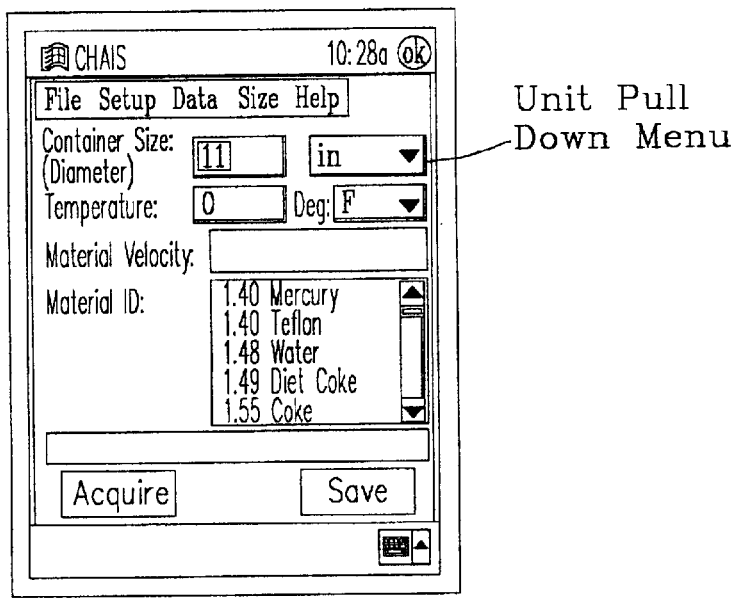

In FIG. 17*c* the down arrow is clicked to access a pull-down menu to select the units.

Figure 17D:
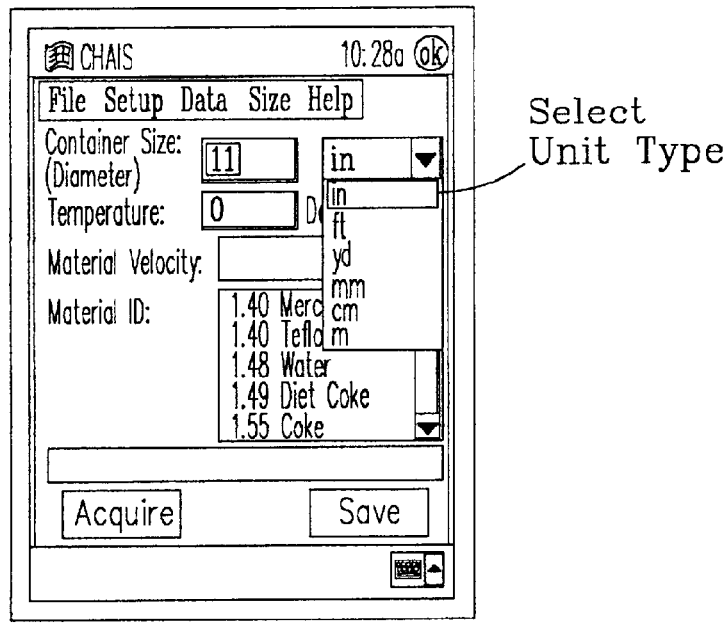

In FIG. 17*d* the appropriate unit type is tapped (for example the "inch" unit is selected).

Figure 17E:
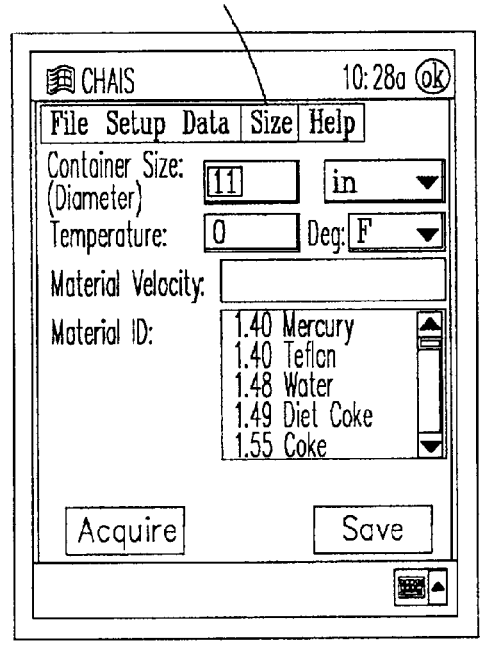

Then in FIG. 17*e* the user taps the "size" button to access a pull-down menu for container types.

Figure 17F:
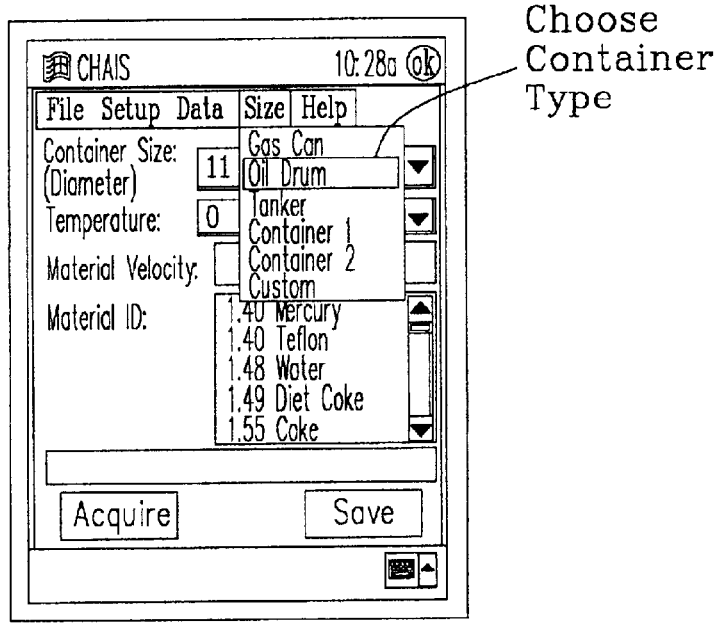

In FIG. 17*f* the appropriate container type button is tapped which in this instance is an oil drum.

Figure 17G:
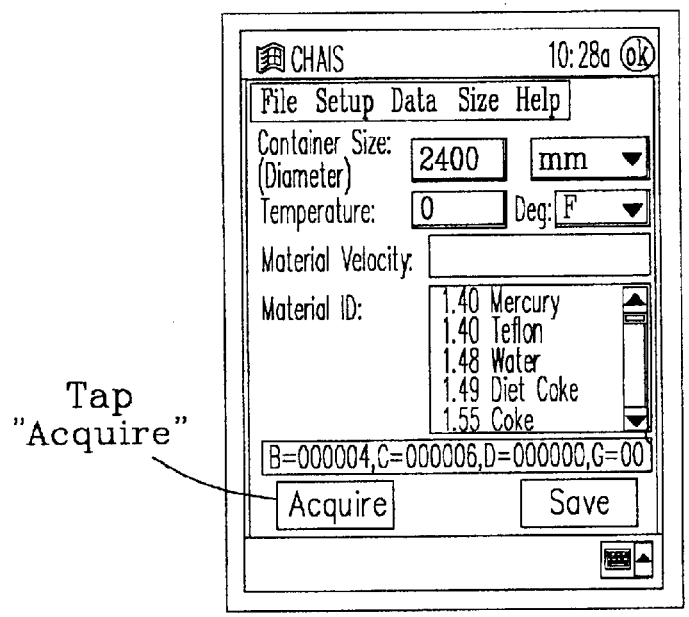

In FIG. 17*g*, the operator (user) is now ready to acquire a waveform, and the "Acquire" button is tapped.

Figure 17H:
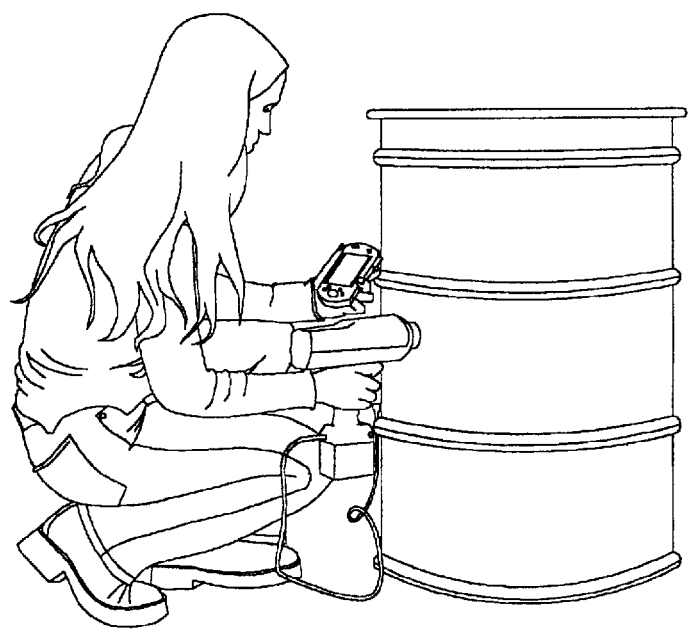
FIG. 17h shows the gun assembly being used to inspect an oil drum.

With the specified values being input, the actual inspection can take place by placing the contact surface 44 of the transducer 40 of the gun assembly 12 against the container that is being inspected and squeezing the trigger 72 to activate the inspection device 12. (See FIG. 17*h*).

In the preferred embodiment, the graphic interface of the host computer 14 should be readily accessible or be able to be viewed by the operator while the gun assembly 12 is in contact with the container. When the trigger 72 is depressed, a series of readings are taken or acquired by the inspection apparatus 10, during which time the operator is able to observe the waveform. It may be that the waveform is somewhat weak or in some other way suspect. If so, the operator could make adjustments to the positioning of the gun to make sure there is proper alignment. Alternatively, the operator can amplify the signal to insure a better display.

Figure 17I:
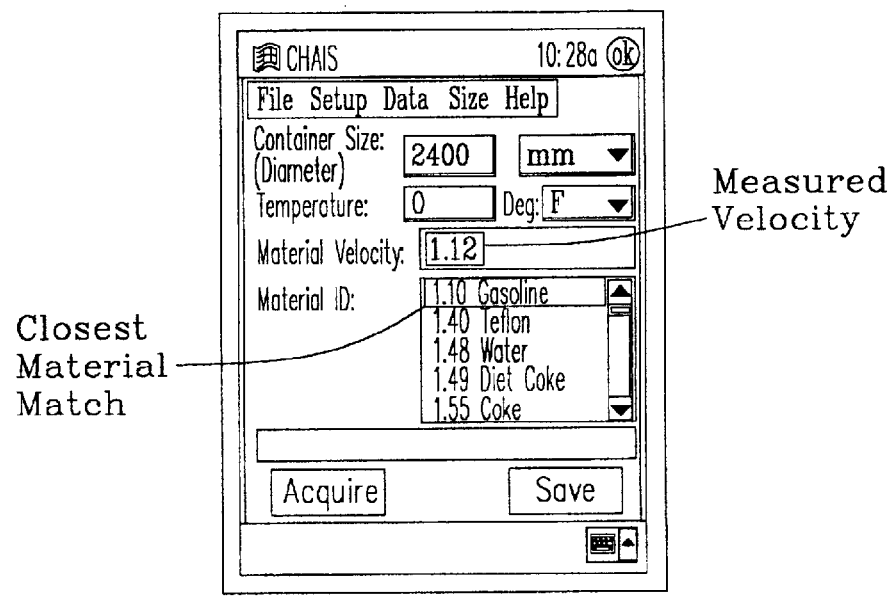
FIGS. 17i, 17j and 17k show the computer interface in three different stages of the inspection process.
Figure 17J:
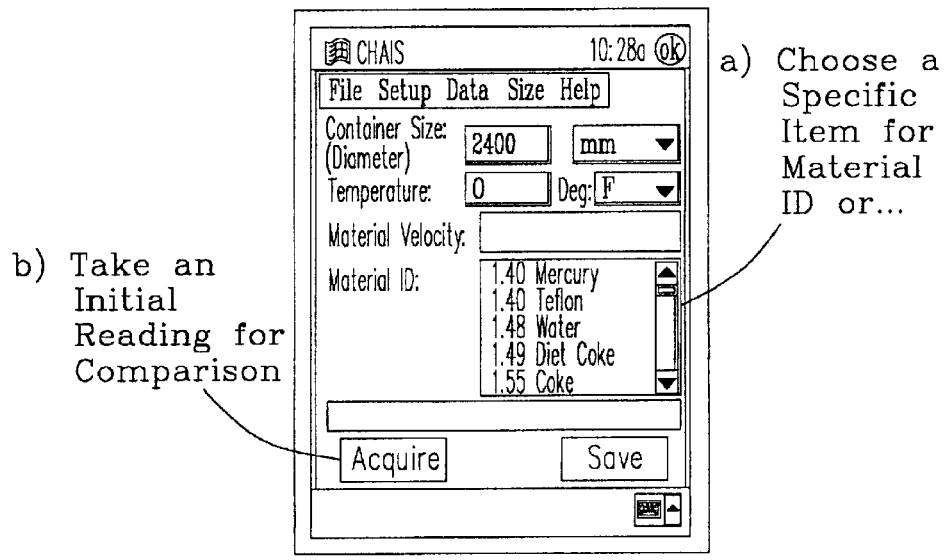

When the trigger 72 of the inspection gun 12 is released, within a few seconds the waveform displayed on screen disappears as the computer computes the appropriate ultrasonic velocity, time-of-flight, and distance determinations. The computer 14 subsequently identifies and displays or otherwise indicates the material being inspected or interrogated by matching the various parameters with the closest material match in the database. As shown in FIG. 17*i*, in this particular instance, the measured velocity is indicated as being 1.12, and the closest material match is indicated as gasoline, which has a velocity of 1.10 Km/second at the measured temperature.

Figure 17K:
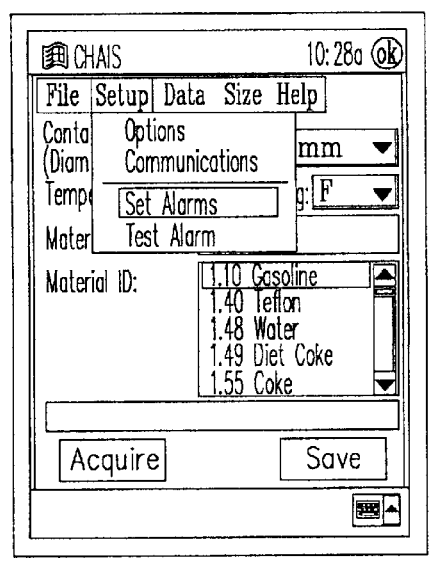

If the inspection is directed particularly toward contraband detection, then the above-described procedure may be modified somewhat. For example, the inspection apparatus 10 may be set to a "Material I.D." or to a "Comparison mode". In the Material I.D. mode, the operator is looking for a specific item (See FIG. 17*i*), while in the Comparison mode the inspector uses an initial reading for comparison with subsequent readings. The Comparison mode may be used in connection with an alarm. In the instance shown with reference to FIG. 17k, there is a "set alarm" section which could be used so that when the discrepancy in the contents of the container is discovered, an alarm signal is communicated and/or provided to the user, either through an audible, visual signal, or both.

Figure 18A:
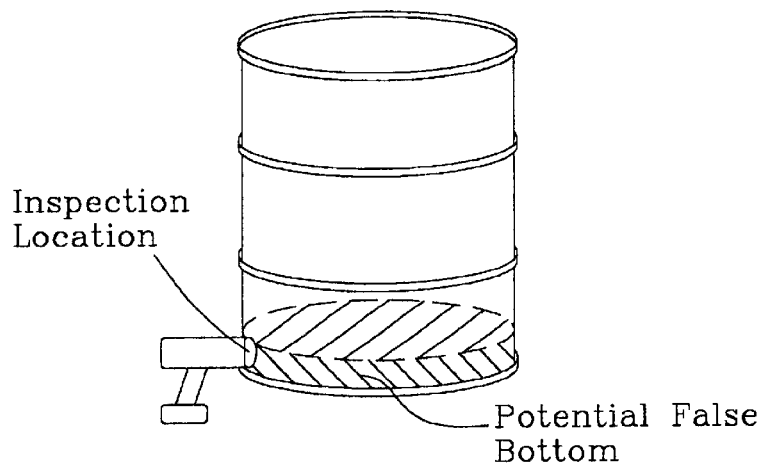
FIG. 18a shows the method of inspecting a drum container for possible foreign objects in the container.
Figure 18B:
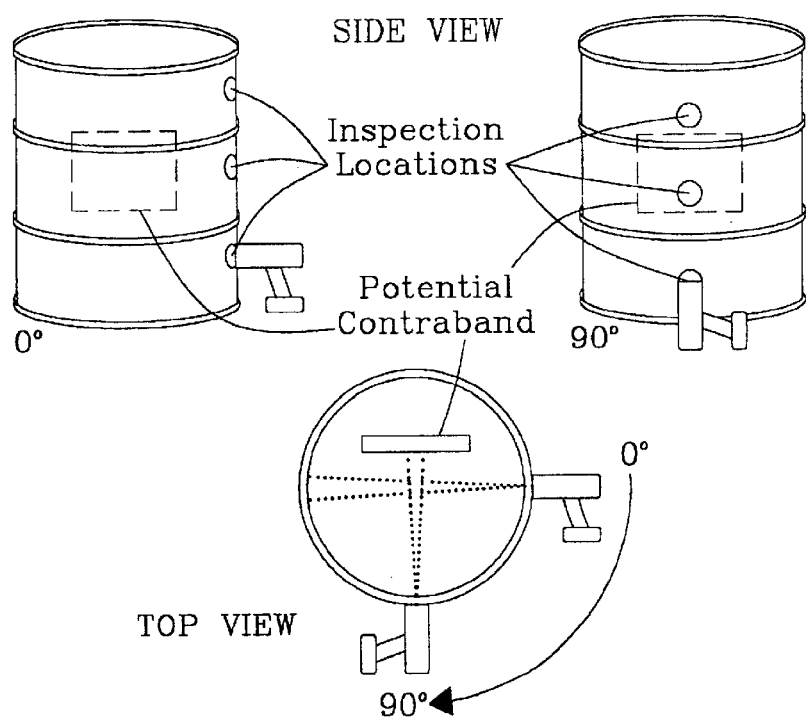
FIG. 18b is another diagram showing another method of inspection for foreign objects in the container.

Various inspection techniques for contraband detection are illustrated in FIGS. 18a and 18b. In FIG. 18a, a barrel is shown being inspected. The gun assembly is first employed near the bottom of the container; the operator works up the side of the container in order to achieve a full volumetric examination of the container. To check the container for a potential false bottom, the inspection gun is placed as low as possible on the side of the container.

In FIG. 18b, a barrel is inspected by directing the ultrasonic beam at a first location, and directing the ultrasonic beam at a second location a distance 90°–120° around the circumference of the drum, such that the ultrasonic beam is directed along a line that is at or near right angles to the first ultrasonic beam. As can be seen in FIG. 18b, this interrogation procedure enhances the chance of detecting a broader surface of the potential contraband.

The above discussion is to show the practical application of the gun assembly 12 being used in conjunction with the computer 14 in an actual inspection operation. Thus, the steps of the method of the present invention are shown, as well as how the host computer 14 may be used (and how the host computer 14 functions) in implementing the preferred method of the present invention.

There will now a more detailed description of how the return signal is processed in the gun assembly 12 and in the computer 14.

As indicated previously, as soon as the transducer 40 emits the ultrasonic pulse, a return wave resulting from the echo at the front wall of the container (the initial portion of the return signal being the "transducer ring down") is immediately initiated, which is followed by the acoustic echo(es). The analog signal from the transducer 40 is received by the receiver board 900, and then transmitted to the digital board 1000 where the analog-to-digital converter 1020 directs the digital output to the FIFO data transmission component 1040 of the digital board 1000. The FIFO 1040 extracts 16,384 samples from the digitized waveform, after which the microcontroller 1030 raises a "digital line" or "digital flag" to signal the PicoWeb™ board 1100 that a new waveform is ready for transmission to the host computer 14. These 16,384 samples are sufficient to encompass the entire return waveform being analyzed.

From the FIFO data component 1040 of the digital board 1000, the digitized signal is transmitted to the PicoWeb™ board 1100 through the PicoWeb™ interface 1010 and PicoWeb™ interface connector 1085 on the digital board 1000, through the parallel I/O connector 1110 on the PicoWeb™ board 1100. Waveform data remain in the FIFO data buffer 1040 until a request is made by the computer 14.

The computer 14 sends a request to the digital board 1000 several times a second to send any digital waveforms that are stored in the FIFO data buffer 1040. The computer 14 may not be able to receive and process waveforms as fast as they can be generated and transferred, so the computer 14 controls the transfer rate by issuing a request for each digital waveform when it (the host computer) 14 is ready.

The digital waveform is transmitted to the PicoWeb™ board 1100, where it is processed and packaged in the microcontroller 1120. Each waveform consists of 16,384 samples, which are divided into 16 packets, to which appropriate transmission protocols (UDP or TCP/IP) are attached. Each packet contains 1,024 one-byte samples and a two-byte packet index. Each packet is given an index count at the front end to keep the 16 packets in order. The packets are then sent along the Ethernet pathway, from the microcontroller 1120 through the Ethernet controller 1130 to the host computer 14. The host computer 14 first examines each packet to ensure that none of the packets is missing and that the packets are in the correct order. The computer 14 then removes the two index count bytes from each packet and reassembles the packets into a complete waveform. The computer 14 then calculates the average amplitude of the samples, and uses this average value as the signal baseline. From this derived baseline, the computer 14 identifies the waveform peaks.

As indicated previously, the waveform typically has periods of noise between peaks. The computer 14 derives the noise level value by generating a histogram of all 16,384 samples. From the histogram, the computer 14 identifies the amplitude level below which 75% of the samples fall. This value is used as the signal noise level for the subsequent calculations.

The next step is to set a threshold level by which the peaks are initially identified This threshold level is located at a programmable amplitude level several times greater than the noise level. In the preferred embodiment, the threshold level is set at five times the noise level, but this value may be adjusted by the operator through the user's interface to compensate for various factors, such as the amount of noise that might be generated, etc. This 75% figure is based upon the assumption that the ring-down plus the peaks in the waveform would not consume more than 25% of the total waveform area.

The next step is to eliminate from the analysis that portion of the waveform in the ring-down zone. This is accomplished as follows.

The computer 14 divides the entire waveform into fifty segments. Each of the samples of the waveform within each of the fifty segments is summed and assigned a value. After this, from the start of the waveform, the computer identifies the first segment that has a total value less than three times the value of the lowest of the summed values. The one or more of the fifty segments that are at the start of the waveform and are higher than that level (i.e. three times the value of the lowest of the sums) is the portion of the wave that is due, or attributed to, the ring-down; the computer will not consider this ring-down portion of the waveform further in the calculations. Calculations are presented and discussed further below.

The next step is to look for and identify peaks in the remaining part of the waveform signal. The computer 14 looks in the initial part of the waveform for any peak that is at least 1.5 times the threshold level (or 1 times the threshold level in the latter part of the waveform). The first peak is initially identified by finding three consecutive samples occurring after the ring-down zone that are greater than one and one-half times the threshold level. When these three consecutive samples are identified, the computer 14 follows the waveform to the trailing edge of the peak dropping below the threshold level. Then the computer 14 sums all the samples beneath that particular peak.

An end-of-peak location is identified when the end portion of the waveform of the peak drops down below the threshold level. The computer 14 continues looking at subsequent samples of the waveform to see if any of these received samples again rises above the threshold level (indicating an additional peak). The number of samples reviewed by the computer would typically be about equal to 0.2 times the number of samples in the ring-down zone. If a number of samples beyond the end-of-peak location are all found to be below the threshold level, the computer will go back to the location where the peak wave initially began to drop below the threshold level and specify that point as the cut-off point location for the waveform.

The computer then adds the absolute value of all samples beneath the peak to derive a total peak value. This same derivation is done for each peak identified in the waveform to distinguish between false peaks and peaks actually resulting from a proper back-wall echo. Thus, if the computer compares two peaks and finds that a second peak has twice the area of the first peak, this would be an indication that the first peak is simply a false peak resulting from the presence of a foreign object within the container. With the location of the "real peaks" having been determined, the computer then computes the time of flight.

Figure 19A:
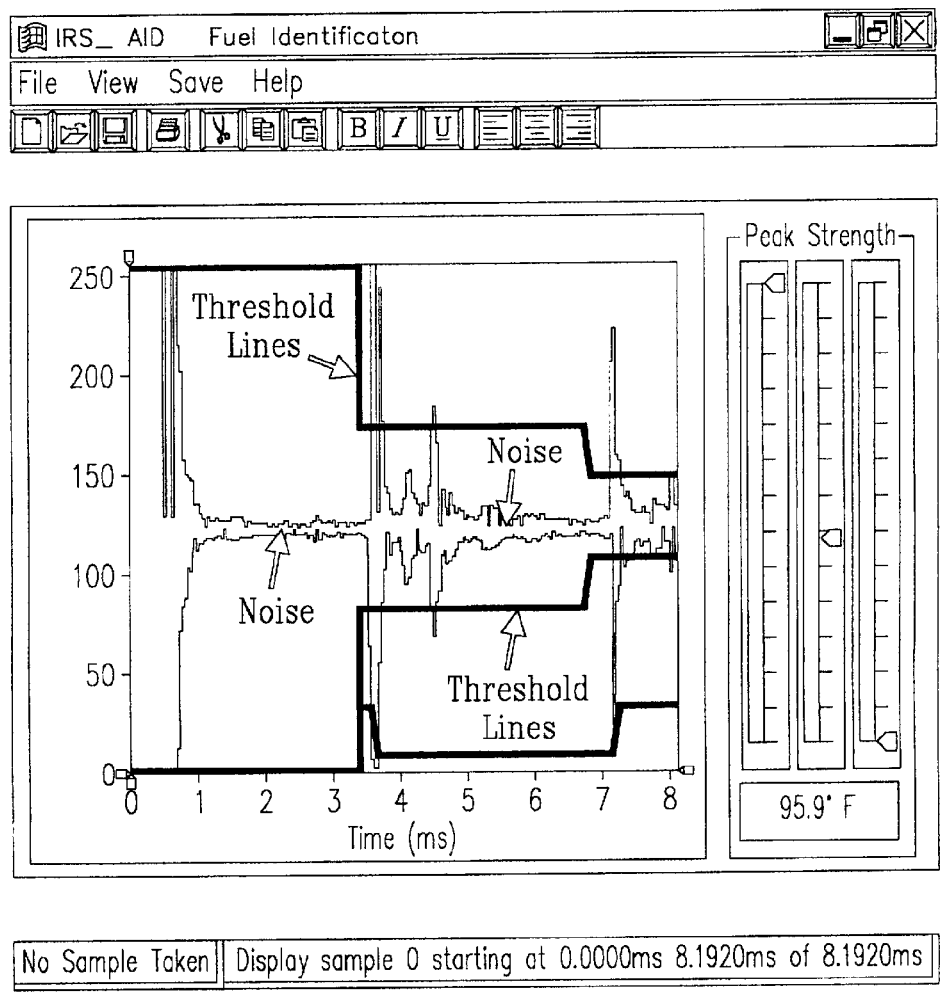
FIGS. 19a to 19d illustrate typical waveforms that would appear on the graphic user interface.

Reference is made to FIG. 19a showing a waveform as it would appear in the graphic interface, with threshold lines shown on the waveform. Threshold lines are provided as a convenience to an operator so that when an operator looks at the waveform displayed on the graphic user interface, the operator is better able to correlate the amplitude of the various parts of the wave to the threshold levels. Further, as shown in FIG. 19a, it will be noted that at the right part of the waveform, a lower threshold level is shown because the second back wall echo generally has a lower amplitude.

Figure 19B:
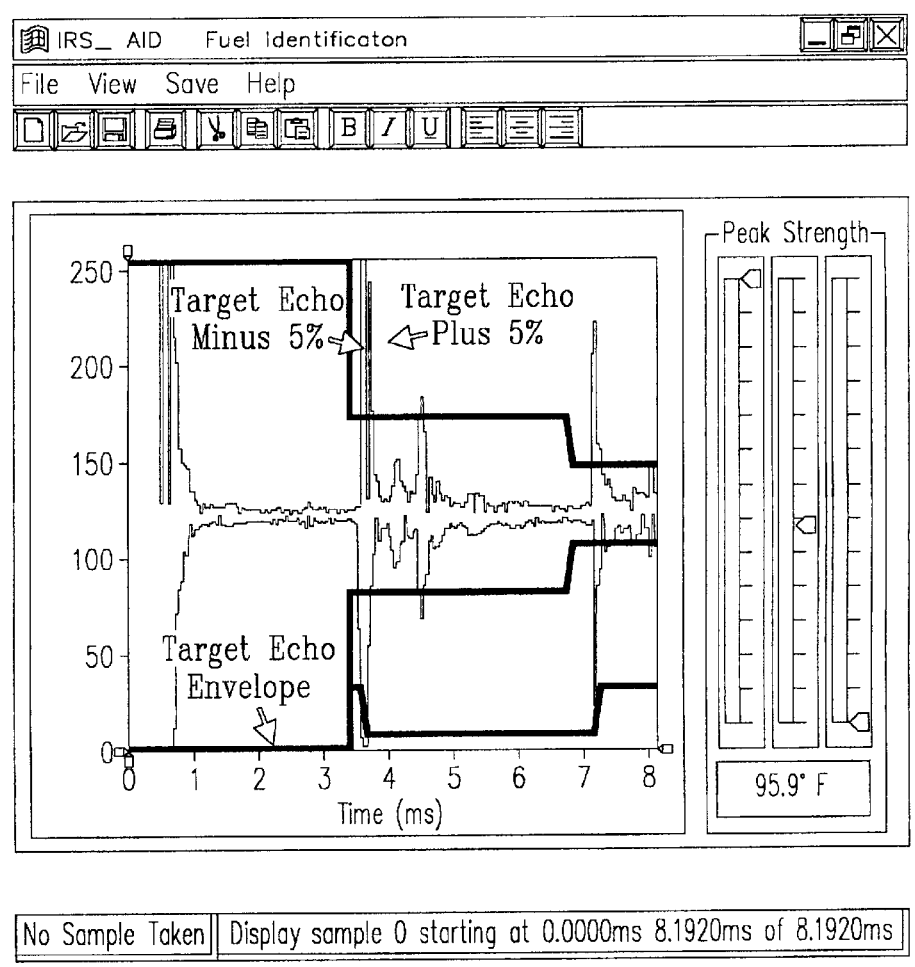

In FIG. 19b essentially the same waveform is shown as in FIG. 19a, but in addition, two vertical target lines are designated, one being in front of the peak amplitude portion of the peak, and the other being on the opposite side of the peak amplitude portion. The vertical target lines are also provided as a guide to an operator.

Figure 19C:
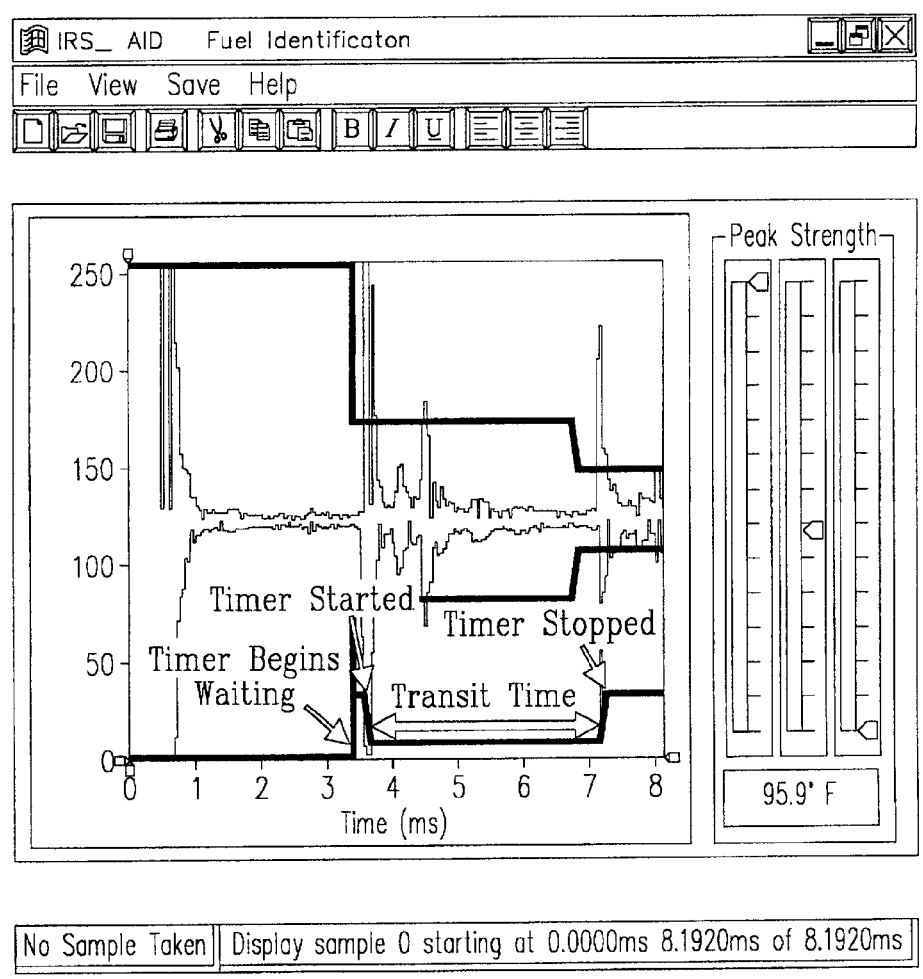

The next step is to measure the time-of-flight of the ultrasonic wave traveling from the front wall to the rear wall of the container, including the return back to the front wall as an acoustic echo. If there is both a first back wall echo and a second back wall echo, in the current embodiment, the time of flight is determined by measuring the time lapse between the first back wall echo and the second back wall echo. In FIG. 19c, time lapse is indicated by the arrow with "transit time" above the arrow. Distance is measured by a correlation technique in which the computer will take the second peak and overlay it with the first peak to see how they correlate with one another, and then the computer can position the two peaks in a way so as to calculate the actual distance between the two peaks.

Figure 19D:
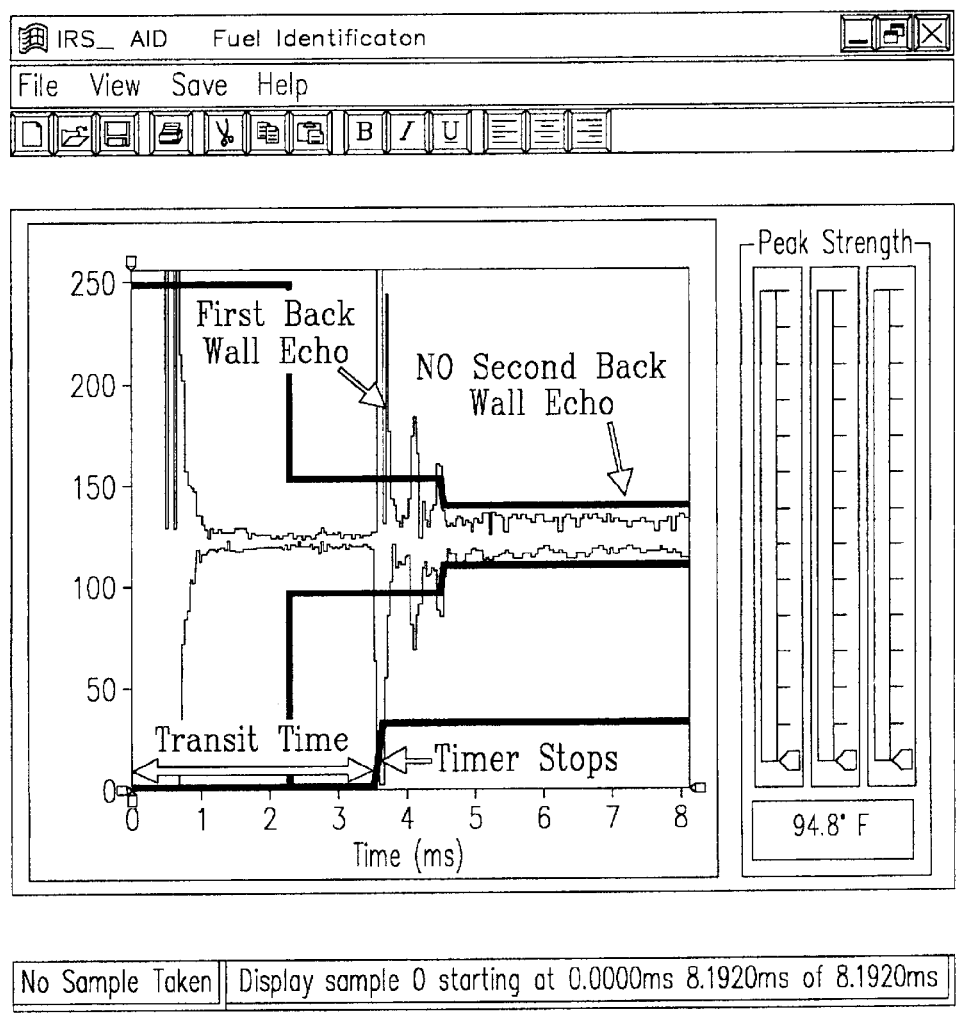

As shown in FIG. 19d, if there is no second back wall echo, or if the back wall echo is of sufficiently low amplitude or otherwise cannot be correlated with the front wall echo, then the transit time is measured from the zero time (the start of the ring-down period) to the front of the first back wall echo.

The arrival time of the first back wall echo can be identified by looking at the first wave segment of the first back wall echo peak that crosses the threshold line, and then following this wave down to the baseline to ascertain the location of the first arrival echo. Alternatively, the first arrival echo could be ascertained by identifying the wave segment having the greatest amplitude and then following it down to the baseline to determine its arrival location.

The measured time-of-flight values for a given waveform are compared with similar database values containing reference information on a large number of reference waveforms. In each case, the time-of-flight reference waveforms are ascertained in the same manner as the readings being taken, thus providing for accurate matches and accurate material identification.

Let us now turn our attention to the manner in which the temperature measurements are incorporated into the velocity calculations. In each interrogation instance, when the transducer is positioned against the side of a container for a reading, temperatures may be in flux, meaning container temperatures may be changing up or down relative to an internal sample material. For example, the transducer may need to be positioned against a surface that has been in a high-temperature environment (i.e., a container sitting in the sun). Thus, it may take time for the surface temperature reading to equalize. Alternatively, there could be a situation in which the ambient temperature is conceivably a stable 60°, while the temperature of the material inside the container could be higher. Because it is important to obtain temperature readings accurately reflecting the temperature of the material within a container (for proper velocity calculations), it is important for operators to wait until temperatures stabilize before taking a final usable reading.

Temperature fluxes in a material or container are indicated by a yellow background in the graphic user interface of the inspection apparatus 10; stable temperatures are indicated by a green background. When determined to be stable, final temperature measurements are taken by the sensor and used to update the velocity table, the update being calculated using a linear equation for velocity as a function of temperature.

It will be noted by examining FIGS. 12 and 13 that the graphic user display indicates (at the right-hand side) both the magnitude of the peak(s) displayed, as well as the temperature value used by the computer for the temperature determinations. Such information allows an operator/user to ascertain whether wait time or other adjustments should be incorporated into a given inspection.

What is claimed:

1. A portably operable ultrasound inspection apparatus particularly adapted to inspect a container which has a containing chamber to contain a quantity of material therein, and which has a front wall and a back wall defining at least in part said containing chamber, said inspection apparatus comprising:

a) a housing section;

b) a sensing section which is mounted to said housing section and which is arranged to transmit transmitted ultrasound pulse(s) and receive reflected ultrasound pulse(s) and to provide an analog signal(s) representative of a reflected waveform(s) of the reflected ultrasonic pulse(s);

c) said sensing section comprising a transducer assembly with a transducer placement location, and at least a first higher frequency transducer and a second lower frequency transducer which are arranged to be better able to transmit pulse(s) in a higher frequency range and in a lower frequency range, respectively, said sensing section being arranged so that either of said transducers can be mounted in said placement location to transmit ultrasound pulses;

d) a circuit section arranged to generate electric pulse(s) for said sensing section, receive the analog signal(s) from said sensing section, and to convert said analog signal(s) to digital signal(s) representative of the reflected waveform(s) of the reflected ultrasonic pulse(s);

e) a temperature sensor to ascertain temperature of the quantity of material in the chamber of the container and provide a temperature output;

f) a computer arranged to receive said digital signal(s) and said temperature output, and to correlate these with travel distance and time of travel of the transmitted pulse(s) and reflected pulse(s) so that with the transmitted pulse(s) and reflected pulse(s) traveling in the chamber of the container, information of velocity of the pulse(s) can be developed and related to identification and/or location of material and/or object(s) in the container.

2. The apparatus as recited in claim 1, wherein said housing comprises a horizontally extending upper housing portion having a front end and a rear end, said sensing section being located at a forward portion of said upper housing portion and said circuit section being located at a rear portion of the upper housing section, said housing further comprising a hand grip portion having an upper end connecting to said upper housing section and a lower end, said apparatus further comprising a trigger section mounted to the hand grip portion so as to be operable by the person manually grasping the hand grip portion.

3. The apparatus as recited in claim 2, wherein the upper end of the hand grip portion is located forwardly of the rear end of the upper housing and rearwardly of the front end of the upper housing, said hand grip portion having a lengthwise alignment axis which extends downwardly from said upper housing portion at a moderate downward and rearward slant from a forward to rear lengthwise alignment axis of said upper housing section.

4. The apparatus as recited in claim 2, wherein said upper horizontally extending housing portion has an upper surface portion thereof configured as a mounting platform on which said computer can be positioned with an upper graphic interface of said computer being readily observable by an operator who is grasping the hand grip portion of the housing.

5. The apparatus as recited in claim 4, wherein said mounting platform to support a computer is positioned on an upper rear surface portion of said upper housing section.

6. The apparatus as recited in claim 2, wherein there is a power supply section for said apparatus, said power supply section being connected to a lower end portion of said hand grip portion of the housing.

7. The apparatus as recited in claim 6, wherein the power supply section is battery powered and said power supply section is removably mounted to said handle grip portion.

8. The apparatus as recited in claim 2, wherein said temperature sensor is located at a forward end portion of the sensing section and is in close proximity to the transducer that is located in the placement location, so that with the transducer being positioned with a contact surface thereof in contact with a container to be inspected, said temperature sensor is also adjacent to a container being inspected.

9. The apparatus as recited in claim 2, wherein each of said transducers is part of a related transducer unit, with each transducer unit comprising a holding case in which the related transducer is positioned and an electrically-connecting portion enabling the transducer to have an operative connection with the circuit section with the transducer being in the placement position.

10. The apparatus as recited in claim 9, wherein each of the transducer units for the first and second transducers is removably mounted in the placement location so that each transducer as part of its related unit is removed from and replaced in the sensing section as a transducer unit.

11. The apparatus as recited in claim 10, wherein there are at least two temperature sensors, with each of the two temperature sensors being a component of a related one of the transducer units and positioned so as to be located at a forward front contact face of its related transducer so as to be able to be in close proximity with a container being inspected by said inspection apparatus.

12. The apparatus as recited in claim 9, wherein said sensing section comprises a transducer unit engaging portion adapted to engage a rear portion of the transducer unit which is in the placement location, said engaging portion having a compression spring which yieldingly engages the transducer unit to urge it to a forward engaging position.

13. The apparatus as recited in claim 12, wherein each of the transducer units for the first and second transducers is removably mounted in the placement location so each transducer as part of each related unit is removed from and replaced in the sensing section as the transducer unit.

14. The inspection apparatus as recited in claim 1, wherein each of said transducers comprises a front contact surface which is arranged to be positioned adjacent to a surface of a container being inspected, and a front contact layer of a synthetic rubber and/or rubber material which covers said front contact surface, said synthetic rubber and/or rubber material being moderately yielding so as to be able to conform to the surface of the container being inspected.

15. The inspection apparatus as recited in claim 14, wherein said front contact layer has an acoustic impedance no greater than 4 gm $cm^{-2}$ $sec^{-1} \times 10^5$, and a longitudinal acoustic velocity between about 0.05 to 0.075 inches per microsecond and a density between about 0.9 to 3.0 gm $cm^{-3}$.

16. The apparatus as recited in claim 15, wherein said acoustic impedance is no greater than 2.5 gm $cm^{-2}$ $sec^{1} \times 10^5$, and said longitudal acoustic velocity is between about 0.06 to 0.065 inches per microsecond and a density is between about 1.2 to 1.5 gm $cm^{-3}$.

17. The inspection apparatus as recited in claim 15, wherein said material for said front contact layer comprises neoprene.

18. The apparatus as recited in claim 14, wherein said front contact layer is made of a material which comprises at least one of solid water, butyl rubber, polyurethane, urethane, RTV, silicone rubber, Ecothane®, Pellathane®, and combinations thereof.

19. The inspection apparatus as recited in claim 14, wherein said front contact layer as an acoustic impedance which is no greater than 4 gm $cm^{-2}$ $sec^{-1} \times 10^5$, and longitudal acoustic velocity which is between about 0.05 to 0.075 inches per microsecond and a density which is between about 0.9 to 3.0 gm $cm^{-3}$ and said front contact layer is made of a material which comprises at least one of solid water, butyl rubber, polyurethane, urethane, RTV, silicone rubber, Ecothane®, Pellathane®, and combinations thereof.

20. The inspection apparatus as recited in claim 19, wherein said liquid adhesive comprises at least in part urethane.

21. The inspection apparatus as recited in claim 14, wherein said front contact layer is bonded to the contact surface of its related transducer by means of a liquid adhesive which is applied between the contact surface of the related transducer and the front contact layer, with the front contact layer being pressed against the adhesive layer and the adhesive layer, and the front contact layer are exposed to a low pressure gaseous environment to cause degassing of the adhesive layer.

22. The inspection apparatus as recited in claim 1, wherein said circuit section comprises a pulser section which has a high frequency pulser circuit portion and a low frequency pulser circuit portion, with these high and low frequency pulser circuit portions being arranged to respond to a high frequency trigger signal or a lower trigger frequency signal to generate, respectively, a high frequency pulse or a low frequency pulse depending upon whether the high frequency transducer or the low frequency transducer is in the transducer placement location.

23. The inspection apparatus as recited in claim 22, wherein said high frequency pulser circuit portion is arranged to receive the high frequency trigger signal, which is directed to a driver circuit that sends a gate signal to a high voltage switch which outputs a high voltage pulse which is in turn directed to the high frequency transducer.

24. The inspection apparatus as recited in claim 22, wherein said high frequency pulse is a square wave pulse.

25. The inspection apparatus as recited in claim 22, wherein said low frequency pulse comprises a sinusoidal burst of a plurality of cycles.

26. The inspection apparatus as recited in claim 1, wherein said circuit section comprises a receiver circuit section which is arranged to receive the analog signal(s) from the sensing section, said receiver circuit section comprising a variable gain amplifier responsive to an input to modify amplitude of the received signal(s).

27. The inspection apparatus as recited in claim 26, wherein said receiver circuit section also comprises a voltage limiter to limit voltage of the received signal(s) to an acceptable level and a high-pass filter to pass only higher frequency portions of the received pulse(s).

28. The inspection apparatus as recited in claim 26, wherein the variable gain amplifier is under the control of the circuit section and also is under control of a user of the inspection apparatus by inputs entered through the computer section.

29. The inspection apparatus as recited in claim 1, wherein said circuit section comprises a signal processing and control section which is arranged to receive the analog signal(s), convert the analog signal(s) to digital signal(s) and to select an adequately large number of samples from the digital signal(s) representing a received waveform(s) of a reflected ultrasound pulse(s), which are then transmitted to the computer.

30. The inspection apparatus as recited in claim 29, wherein said signal processing and control section also functions to send enabling signals to a pulser section of the circuit section to initiate the low frequency and the high frequency pulse(s).

31. The inspection apparatus as recited in claim 1, wherein there is a signal processing and control section which functions to control at least one delay time, digitizing rate, frequency, pulse width, and combinations thereof, of electric pulses being transmitted to the transducers.

32. The inspection apparatus as recited in claim 31, wherein said signal processing and control section further comprises a microprocessor having operative connections to the computer section, and controlling delay time, digitizing rate, frequency of burst, or width of electric pulses and combinations thereof through instructions from the computer, which instructions are capable of being entered by an operator.

33. The inspection apparatus as recited in claim 32, wherein a signal processing and control section further comprises a gate array component having an operative connection with a waveform and analog-to-digital converter of the signal processing and control section to effect the control functions as recited in claim 32.

34. The inspection apparatus as recited in claim 1, wherein there is a signal processing and control section comprising circuitry to receive an analog temperature output from a temperature sensor, said temperature sensor being arranged to sense temperature of material in a container being inspected, and to convert the analog or digital temperature signal.

35. The inspection apparatus as recited in claim 34, wherein the signal processing and control section is responsive to interrogation from an operator utilizing the computer to ascertain from the signal processing and control section temperature readings, and also said computer is arranged to periodically request and receive input temperature readings from the signal processing and control section to the computer.

36. The inspection apparatus as recited in claim 1, wherein said circuit section comprise a RAM component which has an operative connection to the computer section and also to a microcontroller of the signal processing and control section so as to be accessible to an operator utilizing the computer section to enable the operator to operate the microcontroller to obtain information for diagnostic purposes or other purposes.

37. The inspection apparatus as recited in claim 1, wherein there is a display section to provide visual indicator(s) of activation, error and/or power in operation of the inspection apparatus.

38. The inspection apparatus as recited in claim 1, wherein said circuit section further comprises a storage component to retain information when power is shut off so that when an operator starts operation of the inspection apparatus, the same operating parameters of the apparatus will be extant as at the time the inspection apparatus was shut down.

39. The inspection apparatus as recited in claim 38, wherein said storage component comprises an EPROM chip component.

40. The inspection apparatus as recited in claim 1, wherein said circuit section is arranged to receive the analog signal(s) and convert them to digital signals, and said computer is arranged to compute average amplitude of the digital signal and from this establish a base line of the waveform(s) from which to make further computations.

41. The inspection apparatus as recited in claim 40, wherein said apparatus is arranged to select an adequately large number of samples from a signal representing a received waveform and representing a reflected ultrasound pulse, which are then transmitted to the computer, said computer being arranged to identify an amplitude level below which are the amplitudes of a preselected percentage of the samples and to utilize said amplitude of a predetermined percentage of the samples as a noise level amplitude for further calculations.

42. The inspection apparatus as recited in claim 41, wherein said computer is arranged to select a threshold level of signal amplitude which is a predetermined amplitude greater than the noise level amplitude and by which peaks of the waveforms are identified.

43. The inspection apparatus as recited in claim 42, wherein said computer is arranged to select peaks in the waveform(s) to ascertain time intervals in paths of travel between waveform peak portions above the threshold level and initially seeking to identify a time interval between a first back wall echo and a second back wall echo represented in the waveform(s).

44. The inspection apparatus as recited in claim 43, wherein if there is an occurrence where a second back wall echo is not able to be identified, said computer is arranged to then ascertain location of a leading edge portion of the first back wall echo in the waveform(s) for ascertaining a time interval between a forward ring down portion of the waveform and the leading edge portion of the first back wall echo of the waveform.

45. The inspection apparatus as recited in claim 43, wherein said computer is arranged to utilize a correlation technique to correlate said first and second back wall echoes as a means of ascertaining a time interval between the first and second back wall echoes.

46. The inspection apparatus as recited in claim 42, wherein said computer is arranged to ascertain amplitude of peak portion of the waveform(s) and ascertaining an early arriving peak waveform portion(s) of lesser amplitude than a later arriving waveform(s) as a manner of identifying a false echo or echoes in the waveform(s) representing presence of a reflection interface other than a back wall interface.

47. The inspection apparatus as recited in claim 1, wherein said computer is arranged to establish a threshold level of received waveform(s) to identify a time interval(s) between waveform peaks and also a temperature input from the temperature sensor and a travel time input, correlating said time interval(s) and travel distance input to establish a temperature adjusted velocity of ultrasonic pulses.

48. The inspection apparatus as recited in claim 47, wherein said computer has a database of materials and related temperature adjusted ultrasound velocities through the materials, and said computer is arranged to correlate said temperature adjusted velocity of the ultrasonic pulse(s) to identify the material through which the ultrasonic pulse(s) has traveled.

49. The inspection apparatus as recited in claim 48, wherein said computer comprises a user input interface by which at least one of amplitude, burst frequency, pulse width, digitizing rate, and combinations thereof are able to be controlled by the user.

50. The inspection apparatus as recited in claim 49, wherein said computer comprises a graphic display by which the waveform(s) is visibly displayed to the user.

51. The inspection apparatus as recited in claim 50, wherein said computer also has capability of displaying parameters of the received waveform comprising at least one of threshold level(s), noise level(s), waveform portion locations relative to waveform analysis and/or examination, and combinations thereof.

52. The inspection apparatus as recited in claim 47, wherein said computer comprises a graphic display by which the waveform(s) is visibly displayed to the user.

53. The inspection apparatus as recited in claim 52, wherein said computer also has capability of displaying parameters of the received waveform comprising at least one of threshold level(s), noise level(s), waveform portion locations relative to waveform analysis and/or examination, and combinations thereof.

54. The inspection apparatus as recited in claim 1, wherein said computer comprises a user input interface by which at least one of amplitude, first frequency, pulse width, digitizing rate, and combinations thereof are able to be controlled by the user.

55. An ultrasound inspection apparatus particularly adapted to inspect a container in a process line, wherein said container has a containing chamber to contain a quantity of material therein, and which has a front wall and a back wall defining at least in part said containing chamber, said inspection apparatus comprising:

a) a housing section;

b) a sensing section which is mounted to said housing section and which is arranged to transmit transmitted ultrasound pulse(s) and receive reflected ultrasound pulse(s) and to provide an analog signal(s) representative of a reflected waveform(s) of the reflected ultrasonic pulse(s);

c) a sensing section comprising a transducer assembly with a transducer placement location, and at least a first higher frequency transducer and a second lower frequency transducer which are arranged to be better able to transmit pulse(s) in a higher frequency range and in a lower frequency range, respectively, said sensing section being arranged so that either of said transducers can be mounted in said placement location to transmit ultrasound pulses;

d) a circuit section arranged to generate electric pulse(s) for said sensing section, receive the analog signal(s) from said sensing section, and to convert said analog signal(s) to digital signal(s) representative of the reflected waveform(s) of the reflected ultrasonic pulse (s);

e) a temperature sensor to ascertain temperature of the quantity of material in the chamber of the container and provide a temperature output;

f) a computer arranged to receive said digital signal(s) and said temperature output, and to correlate these with travel distance and time of travel of the transmitted pulse(s) and reflected pulse(s) so that with the transmitted pulse(s) and reflected pulse(s) traveling in the chamber of the container, information of velocity of the pulse(s) is able to be developed and related to identification and/or location of material and/or object(s) in the container.

* * * * *